United States Patent
Chen et al.

(10) Patent No.: US 11,580,641 B1
(45) Date of Patent: Feb. 14, 2023

(54) DEEP LEARNING BASED METHODS AND SYSTEMS FOR NUCLEIC ACID SEQUENCING

(71) Applicant: GeneSense Technology Inc., Shanghai (CN)

(72) Inventors: Gengxin Chen, Pudong District (CN); Shaobo Luo, Shenzheng (CN); Shuwei Li, Shenzheng (CN); Jichao Yan, Shanghai (CN); Tianzhen Ao, Shanghai (CN); Yuan Lu, Shanghai (CN); Mei Yan, Shanghai (CN)

(73) Assignee: GeneSense Technology Inc., Shanghai (CN)

( * ) Notice: Subject to any disclaimer, the term of this patent is extended or adjusted under 35 U.S.C. 154(b) by 0 days.

(21) Appl. No.: 17/681,672

(22) Filed: Feb. 25, 2022

Related U.S. Application Data

(63) Continuation of application No. PCT/CN2021/141269, filed on Dec. 24, 2021.

(51) Int. Cl.
  G06K 9/00 (2022.01)
  A61B 5/05 (2021.01)
  (Continued)

(52) U.S. Cl.
  CPC ......... G06T 7/0012 (2013.01); G06N 3/0472 (2013.01); G06N 3/063 (2013.01);
  (Continued)

(58) Field of Classification Search
  CPC .................................. G06K 9/00; A61B 5/05
  (Continued)

(56) References Cited

U.S. PATENT DOCUMENTS

| | | |
|---|---|---|
| 10,540,591 B2 | 1/2020 | Gao et al. |
| 11,200,446 B1 | 12/2021 | Zhou et al. |

(Continued)

FOREIGN PATENT DOCUMENTS

| | | |
|---|---|---|
| CN | 110892484 A | 3/2020 |
| CN | 112313750 A | 2/2021 |

(Continued)

OTHER PUBLICATIONS

Xu et al., "Fast-Bonito: A Faster Basecaller for Nanopore Sequencing," BioRxiv, 2020, 10 pages.

(Continued)

*Primary Examiner* — Seyed H Azarian
(74) *Attorney, Agent, or Firm* — Mauriel Kapouytian Woods LLP; Liang Huang

(57) ABSTRACT

Methods and systems for determining a plurality of sequences of nucleic acid (e.g., DNA) molecules in a sequencing-by-synthesis process are provided. In one embodiment, the method comprises obtaining images of fluorescent signals obtained in a plurality of synthesis cycles. The images of fluorescent signals are associated with a plurality of different fluorescence channels. The method further comprises preprocessing the images of fluorescent signals to obtain processed images. Based on a set of the processed images, the method further comprises detecting center positions of clusters of the fluorescent signals using a trained convolutional neural network (CNN) and extracting, based on the center positions of the clusters of fluorescent signals, features from the set of the processed images to generate feature embedding vectors. The method further comprises determining, in parallel, the plurality of sequences of DNA molecules using the extracted features based on a trained attention-based neural network.

26 Claims, 17 Drawing Sheets

(51) Int. Cl.
*G06T 7/00* (2017.01)
*G06V 10/82* (2022.01)
*G06V 10/77* (2022.01)
*G06T 7/70* (2017.01)
*G06T 5/00* (2006.01)
*G06T 7/13* (2017.01)
*G06N 3/063* (2023.01)
*G06N 3/04* (2023.01)
*G06T 7/38* (2017.01)

(52) U.S. Cl.
CPC .............. *G06T 5/002* (2013.01); *G06T 5/009* (2013.01); *G06T 7/13* (2017.01); *G06T 7/38* (2017.01); *G06T 7/70* (2017.01); *G06V 10/7715* (2022.01); *G06V 10/82* (2022.01); *G06T 2207/10064* (2013.01); *G06T 2207/20076* (2013.01); *G06T 2207/20084* (2013.01); *G06V 2201/04* (2022.01)

(58) Field of Classification Search
USPC ....... 382/100, 103, 128–134, 156, 168, 173, 382/181, 190, 214, 219, 223–224, 254, 382/276, 286–291, 305; 600/408
See application file for complete search history.

(56) References Cited

U.S. PATENT DOCUMENTS

| | | | |
|---|---|---|---|
| 2019/0237160 A1 | 8/2019 | Rothberg et al. | |
| 2020/0109446 A1* | 4/2020 | Finkelstein | C12Q 1/6837 |
| 2020/0167914 A1* | 5/2020 | Stamatoyannopoulos | G06T 7/0012 |
| 2020/0176082 A1 | 6/2020 | Massingham | |
| 2020/0327377 A1* | 10/2020 | Jaganathan | G06K 9/6222 |
| 2022/0044074 A1* | 2/2022 | Li | G06T 7/0002 |
| 2022/0076787 A1* | 3/2022 | Ellington | G16B 15/20 |

FOREIGN PATENT DOCUMENTS

| | | |
|---|---|---|
| GB | 2600719 A | 5/2022 |
| WO | 2020/191391 A2 | 9/2020 |

OTHER PUBLICATIONS

International Search Report and Written Opinion issued in International Application No. PCT/CN2021/141269 dated Sep. 21, 2022, 9 pages.

* cited by examiner

DEEP LEARNING BASED METHODS AND SYSTEMS FOR NUCLEIC ACID SEQUENCING

CROSS REFERENCE TO RELATED APPLICATIONS

This application is a continuation application of International Application Number PCT/CN2021/141269 filed on Dec. 24, 2021. The entire content of the application is hereby incorporated herein by reference for all purposes.

FIELD OF TECHNOLOGY

The present disclosure relates generally to nucleic acid sequencing, and more specifically to systems, devices, and methods for basecalling using deep learning models for analyzing fluorescent signal data in a sequencing-by-synthesis process.

BACKGROUND

Sequencing-by-synthesis is a method used to identify sequences of segments (also referred to as strands) of nucleic acid (e.g., DNA) molecules. Sanger sequencing is a first-generation sequencing technique that uses the sequencing-by-synthesis method. Historically, Sanger sequencing has a high degree of accuracy but is low in sequencing throughput. Second-generation sequencing techniques (also referred to as next generation sequencing or NGS techniques) massively increase the throughput of the synthesizing process by parallelizing many reactions similar to those in Sanger sequencing. Third-generation sequencing techniques allow direct sequencing of single nucleic acid molecules. In any of the sequencing technology generations, basecalling is an essential process by which an order of the nucleotide bases in a template strand is inferred during or after a sequencing readout.

SUMMARY

Next generation sequencing techniques (and other future generation sequencing techniques) can massively increase the throughput of the synthesis process and therefore generate a massive amount of data for basecalling. The processing of the massive amount of data remains challenging. For example, the massive number of fluorescent signals and the varying noise signals impose difficulties for traditional algorithms to distinguish signals of clusters that are located very close to each other. Furthermore, during a sequencing process, there are crosstalk between different fluorescent signal channels and loss of synchrony in cluster molecules (also referred to as cluster phasing and prephasing). The loss of synchrony in cluster molecules are caused by stochastic nature of chemical reactions and other factors in which some molecules may fail to incorporate a labelled nucleotide whereas some other molecules may incorporate more than one nucleotide. This results in leakage in signal intensity between cycles. The crosstalk and loss in synchrony in turn cause difficulties in predicting nucleotide bases. Recently, machine learning models have been developed for basecalling. Existing machine learning models use, for example, a combination of a traditional convolutional neural network (CNN) and a recurrent neural network (RNN) network. The CNN is for performing image analysis to detect clusters of fluorescent signals and the RNN is for processing sequence data. Basecalling using these existing machine learning models, however, still face many challenges. For example, they may be time consuming, computationally complex, and demand a large amount of computing resources. In addition, they may not provide a satisfactory basecalling accuracy. Thus, there is a need for systems and methods using improved machine learning models that can provide higher efficiency and higher accuracy while requiring less computational resources and time.

The embodiments of the present invention provide basecalling methods and systems using a combination of various image preprocessing algorithms, improved cluster detection algorithms and signal extraction algorithms, and attention-based or 1D convolution-based neural network models. The image preprocessing algorithms preprocess fluorescence images to generate enhanced images for easier cluster detection. The enhanced images are provided to a deep learning based cluster detection model to find the clusters represented in the images. The cluster detection model increases the cluster detection speed and provides more robust and accurate cluster detection results. One-dimensional or two-dimensional signal extraction is then performed using the detected clusters to obtain feature embedding vectors for basecalling.

For basecalling, embodiments of the present invention use several attention-based deep learning models. The attention-based models can include, for example, a transformer neural network model. RNN models have been used in the past for basecalling, but they generally do not process input data in parallel. However, attention-based deep learning models are better suited to parallel processing. Specifically, attention-based models generate attention vectors that are independent from one another. Therefore, they can be processed in parallel, significantly improving the basecalling speed. The amount of image data generated during a synthesis process is directly proportional to the length of a sequence. Thus, attention-based deep learning models are particularly efficient in processing long sequences because of their capabilities of processing input data in parallel. Due to the attention mechanism, an attention-based model also better explains the relation between the input data elements. As a result, attention-based models also improve the basecalling accuracy or reduce the error rate. Various embodiments of the basecalling algorithms described herein can be applied for nucleic acid sequencing (e.g., DNA sequencing, RNA sequencing, artificial nucleic acid sequencing) and/or protein sequencing.

Embodiments of the present invention improve and optimize the speed and accuracy of cluster detection and basecalling. The embodiments further provide an intelligent and automated way to perform data labelling, thereby reducing the burden of manual labelling effort. The embodiments further improve computer efficiency. For example, the time for cluster detection may be reduced by about 33% and the time for basecalling may be reduced by about 50%.

In some embodiments of the invention, a computer-implemented method for determining a plurality of sequences of nucleic acid (e.g., DNA) molecules in a sequencing-by-synthesis process is provided. The method comprises obtaining images of fluorescent signals obtained in a plurality of synthesis cycles. The images of fluorescent signals are associated with a plurality of different fluorescence channels. The method further comprises preprocessing the images of fluorescent signals to obtain processed images. Based on a set of the processed images, the method further comprises detecting center positions of clusters of the fluorescent signals using a trained convolutional neural network (CNN) and extracting, based on the center positions of the clusters of fluorescent signals, features from the set of the processed images to generate feature embedding vectors. The method further comprises determining, in parallel, the plurality of sequences of DNA molecules using the extracted features based on a trained attention-based neural network.

In some embodiments of the invention, a computer-implemented method for determining a plurality of sequences of nucleic acid (e.g., DNA) molecules in a sequencing-by-synthesis process is provided. The method comprises obtaining images of fluorescent signals obtained in a plurality of synthesis cycles. The images of fluorescent signals are associated with a plurality of different fluorescence channels. The method further comprises preprocessing the images of fluorescent signals to obtain processed images. The method further comprises based on a set of the processed images, detecting center positions of clusters of the fluorescent signals using a trained convolutional neural network (CNN). The method further comprises extracting, based on the center positions of the clusters of fluorescent signals, features from the set of the processed images to generate feature embedding vectors. The method further comprises determining, in parallel, the plurality of sequences of nucleic acid molecules using the extracted features based on a trained 1-dimensional convolution-based neural network.

In some embodiments of the invention, a computer-implemented method for training one or more neural networks used in a process of determining a plurality of sequences of nucleic acid (e.g., DNA) molecules in a sequencing-by-synthesis process is provided. The method comprises obtaining images of fluorescent signals obtained in a plurality of synthesis cycles. The images of fluorescent signals are associated with a plurality of different fluorescence channels. The method further comprises preprocessing the images of fluorescent signals to obtain processed images. The method further comprises extracting signal intensities of the fluorescent signals at selected areas of the processed images. Based on the extracted signal intensities, the method further comprises performing basecalling by using a known basecalling algorithm to obtain predicted nucleic acid sequences. The method further comprises training the one or more neural networks using the predicted nucleic acid sequences.

These and other embodiments are described more fully below.

Figure 1:
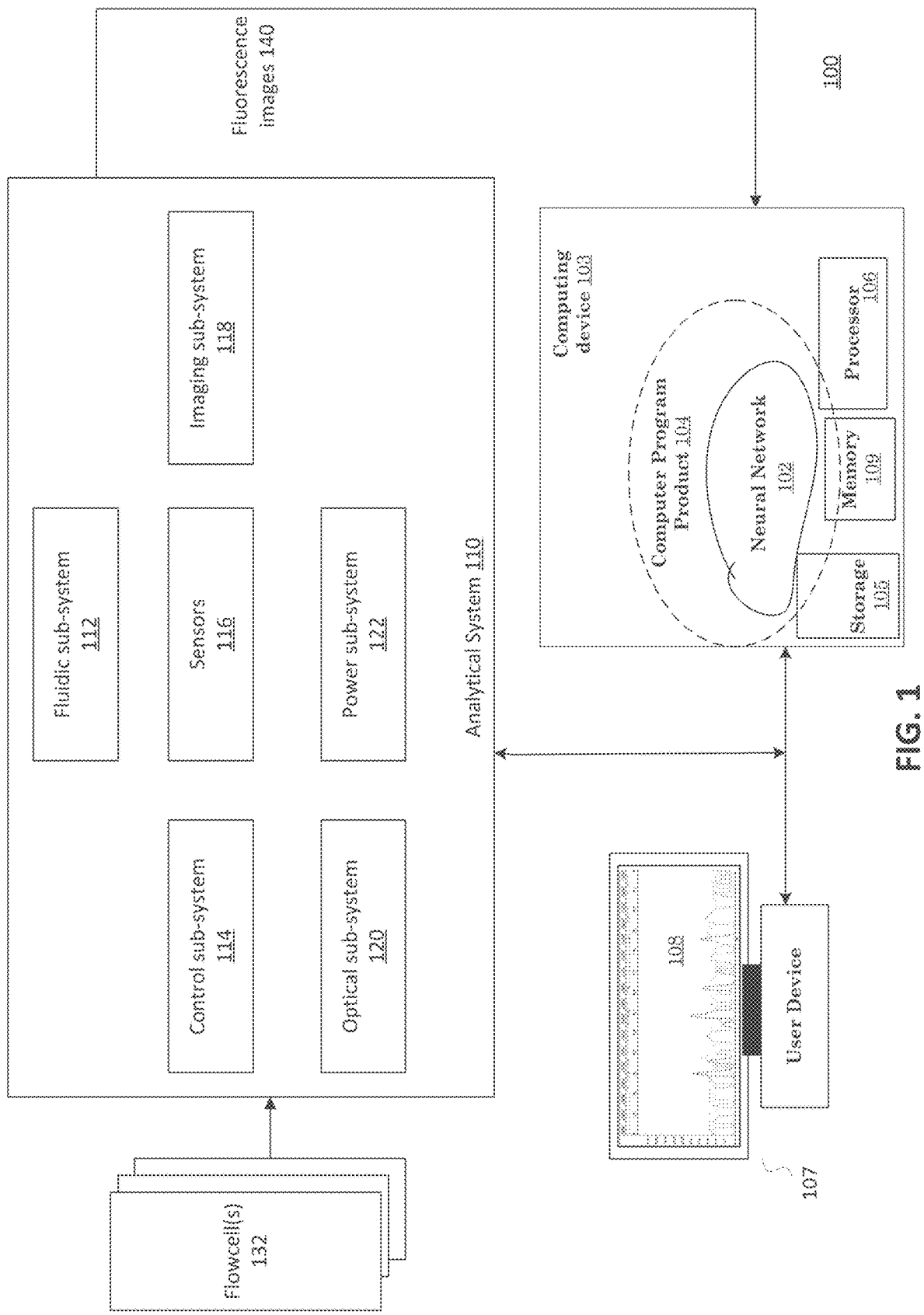
FIG. 1 illustrates an exemplary next generation sequencing (NGS) system in accordance with an embodiment of the present invention.

While the embodiments of the present invention are described with reference to the above drawings, the drawings are intended to be illustrative, and other embodiments are consistent with the spirit, and within the scope, of the invention.

DETAILED DESCRIPTION

The various embodiments now will be described more fully hereinafter with reference to the accompanying drawings, which form a part hereof, and which show, by way of illustration, specific examples of practicing the embodiments. This specification may, however, be embodied in many different forms and should not be construed as limited to the embodiments set forth herein; rather, these embodiments are provided so that this specification will be thorough and complete, and will fully convey the scope of the invention to those skilled in the art. Among other things, this specification may be embodied as methods or devices. Accordingly, any of the various embodiments herein may take the form of an entirely hardware embodiment, an entirely software embodiment or an embodiment combining software and hardware aspects. The following specification is, therefore, not to be taken in a limiting sense.

As described above, analyzing a massive number of fluorescent signals produced by NGS techniques imposes several challenges. For example, existing NGS systems may use a two-dimensional spot detection for determination of clusters of fluorescent signals. The traditional algorithms used for such a cluster determination have difficulties in distinguishing the nucleic acid bases when the clusters are located close to one another. Moreover, noise collected by the systems may vary from time to time, making the detection process less robust. The crosstalk between different fluorescence channels and/or loss of synchrony in cluster molecules may further negatively impact the prediction of the nucleic acid bases.

Traditional basecalling technologies use conventional image process and statistical models to derive features from the input image data. Recently, machine learning based systems are developed. But users need to manually design features and choose classifiers. More recently, deep learning based basecalling techniques have also been developed. For example, cluster detection for basecalling uses several machine learning based approaches (e.g., K-Mean, Fully Convolutional Network or FCN, and U-Net). For basecalling of each cluster, statistical models (e.g., the AYB model) and several Recurrent Neural Network (RNN) based models are used. These RNN based models include, for example, a Long Short-Term Memory network (LSTM), a bidirectional LSTM (Bi-LSTM), a Gated Recursive Unit (GRU), and/or a Connectionist Temporal Classification (CTC).

In the existing technologies, the image analysis performance, the cluster detection speed and accuracy, and the basecalling speed and accuracy may not satisfy user requirements. In some cases, for example, the neural network used is computationally complex. Therefore, the cluster detection and/or the basecalling process may take a very long time to complete and may thus be inefficient. Moreover, in some cases, if the speed is improved, the basecalling accuracy may be sacrificed. Additionally, training a conventional neural network used for basecalling may require a massive effort of manual data labelling, which may be impractical.

Embodiments of the present invention discussed herein provide an enhanced deep learning neural network pipeline, which uses various image processing and enhancement techniques, a new CNN-based neural network model for cluster detection, and an attention-based deep learning model or an 1D convolution-based deep learning model for basecalling. The methods described herein improve and optimize the speed and accuracy of cluster detection and basecalling. The methods further provide an intelligent and automated way to perform data labelling, thereby reducing the burden of manual labelling effort. Details of the embodiments of the present invention are described below.

Next Generation (and Future Generations) Sequencing System

FIG. 1 is a block diagram illustrating an exemplary analytical system 110. As illustrated in FIG. 1, analytical system 110 includes an optical sub-system 120, an imaging sub-system 118, a fluidic sub-system 112, a control sub-system 114, sensors 116, and a power sub-system 122. Analytical system 110 can be used to perform next-generation sequencing (NGS) reactions and produce fluorescence images 140 captured during multiple synthesis cycles. These images 140 are provided to computer(s) 103 for basecalling.

Figure 2:
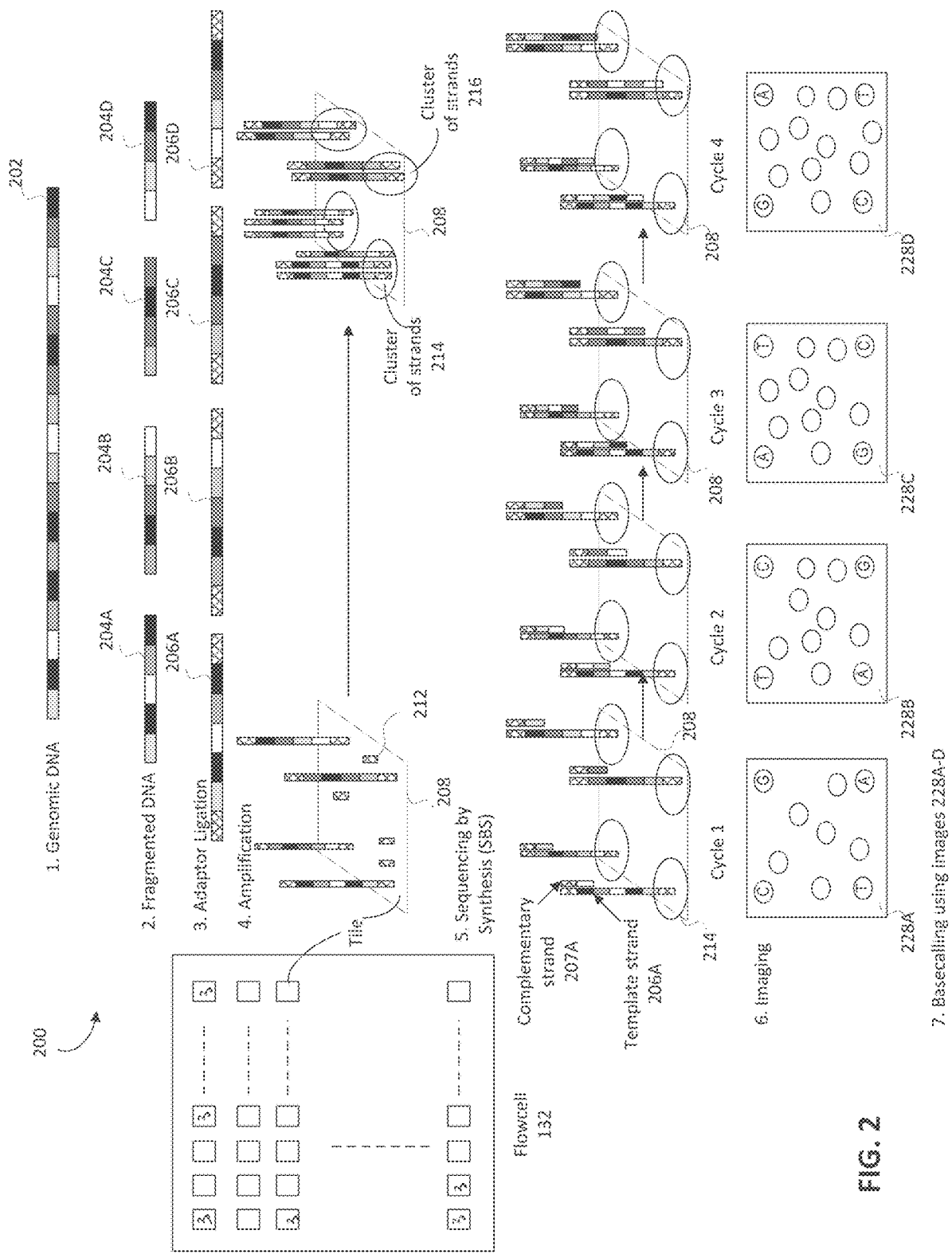
FIG. 2 illustrates an exemplary sequencing-by-synthesis process using an NGS system in accordance with an embodiment of the present invention.

Referencing FIG. 1, one or more flowcell(s) 132 are provided to analytical system 110. A flowcell is a slide with fluidic channels or lanes, where the sequencing reactions occur. In some embodiments, each fluidic channel of a flowcell includes an array of tiles. Each tile may have numerous clusters generated on the surface and forms a logical unit for imaging and data processing. FIG. 2 illustrates a flowcell 132 having multiple tiles and also illustrates an exemplary tile 208. The synthesis process occurs in flowcell 132 and is described below in more detail.

Referencing FIG. 1, optical sub-system 120, imaging sub-system 118, and sensors 116 are configured to perform various functions including providing an excitation light, guiding or directing the excitation light (e.g., using an optical waveguide), detecting light emitted from samples as a result of the excitation light, and converting photons of the detected light to electrical signals. For example, optical sub-system 120 includes an excitation optical module and one or more light sources, an optical waveguide, and/or one or more filters. In some embodiments, the excitation optical module and the light source(s) include laser(s) and/or light-emitting diode (LED) based light source(s) that generate and emit excitation light. The excitation light can have a single wavelength, a plurality of wavelengths, or a wavelength range (e.g., wavelengths between 200 nm to 1600 nm). For instance, if system 110 has a four-fluorescence channel configuration, optical sub-system 120 uses four different fluorescent lights having different wavelengths to excite four different corresponding fluorescent dyes (one for each of the bases A, G, T, C).

In some embodiments, the excitation optical module can include further optical components such as beam shaping optics to form uniform collimated light. The excitation optical module can be optically coupled to an optical waveguide. For example, one or more of grating(s), mirror(s), prism(s), diffuser(s), and other optical coupling devices can be used to direct the excitation lights from the excitation optical module toward the optical waveguide.

In some embodiments, the optical waveguide can include three parts or three layers—a first light-guiding layer, a fluidic reaction channel, and a second light-guiding layer. The fluidic reaction channel may be bounded by the first light-guiding layer on one side (e.g., the top side) and bounded by the second light-guiding layer on the other side (e.g., the bottom side). The fluidic reaction channel can be used to dispose flowcell(s) 132 bearing the biological sample. The fluidic reaction channel can be coupled to, for example, fluidic pipelines in fluidic sub-system 112 to receive and/or exchange liquid reagent. A fluidic reaction channel can be further coupled to other fluidic pipelines to deliver liquid reagent to the next fluidic reaction channel or a pump/waste container.

In some embodiments, the fluorescent lights are delivered to flowcell(s) 132 without using an optical waveguide. For example, the fluorescent lights can be directed from the excitation optical module to flowcell(s) 132 using free-space optical components such as lens, grating(s), mirror(s), prism(s), diffuser(s), and other optical coupling devices.

As described above, fluidic sub-system 112 delivers reagents to flowcell(s) 132 directly or through a fluidic reaction channel using fluidic pipelines. Fluidic sub-system 112 performs reagent exchange or mixing, and dispose waste generated from the liquid photonic system. One embodiment of fluidic sub-system 112 is a microfluidics sub-system, which can process small amount of fluidics using channels measuring from tens to hundreds of micrometers. A microfluidics sub-system allows accelerating PCR processes, reducing reagent consumption, reaching high throughput assays, and integrating pre- or post-PCR assays on-chip. In some embodiments, fluidic sub-system 112 can include one or more reagents, one or more multi-port rotary valves, one or more pumps, and one or more waste containers.

The one or more reagents can be sequencing reagents in which sequencing samples are disposed. Different reagents can include the same or different chemicals or solutions (e.g., nucleic acid primers) for analyzing different samples. Biological samples that can be analyzed using the systems described in this application include, for example, fluorescent or fluorescently-labeled biomolecules such as nucleic acids, nucleotides, deoxyribonucleic acid (DNA), ribonucleic acid (RNA), peptide, or proteins. In some embodiments, fluorescent or fluorescently-labeled biomolecules include fluorescent markers capable of emitting light in one, two, three, or four wavelength ranges (e.g., emitting red and yellow lights) when the biomolecules are provided with an excitation light. The emitted light can be further processed (e.g., filtered) before they reach the image sensors.

With reference to FIG. 1, analytical system 110 further includes a control sub-system 114 and a power sub-system 122. Control sub-system 114 can be configured (e.g., via software) to control various aspects of the analytical system 110. For example, control sub-system 114 can include hardware and software to control the operation of optical sub-system 120 (e.g., control the excitation light generation), fluidic sub-system 112 (e.g., control the multi-port rotary valve and pump), and power sub-system 122 (e.g., control the power supply of the various systems shown in FIG. 1). It is understood that various sub-systems of analytical system 110 shown in FIG. 1 are for illustration only. Analytical system 110 can include more or fewer sub-systems than shown in FIG. 1. Moreover, one or more sub-systems included in analytical system 110 can be combined, integrated, or divided in any manner that is desired.

Referencing FIG. 1, analytical system 110 includes sensor(s) 116 and an imaging sub-system 118. Sensor(s) 116 detect photons of light emitted from the biological sample and convert the photons to electrical signals. Sensor(s) 116 are also referred to as image sensor(s). An image sensor can be a semiconductor-based image sensor (e.g., silicon-based CMOS sensor) or a charge-coupled device (CCD) image sensor. A semiconductor-based image sensor can be a backside illumination (BSI) based image sensor or a front side illumination (FSI) based image sensor. In some embodiments, sensor(s) 116 may include one or more filters to remove scattered light or leakage light while allowing a substantial portion of the light emitted from the biological sample to pass. Filters can thus improve an image sensor's signal-to-noise ratio.

The photons detected by sensor(s) 116 are processed by imaging sub-system 118. An imaging sub-system 118 includes a signal processing circuitry, which is electrically coupled to sensor(s) 116 to receive electrical signals generated by sensor(s) 116. In some embodiments, the signal processing circuitry can include one or more charge storage elements, an analog signal readout circuitry, and a digital control circuitry. In some embodiments, the charge storage elements receive or read out electrical signals generated in parallel based on substantially all photosensitive elements of an image sensor 116 (e.g., using a global shutter); and transmit the electrical signals to the analog signal read-out circuitry. The analog signal read-out circuitry may include, for example, an analog-to-digital converter (ADC), which converts analog electrical signals to digital signals.

In some embodiments, after the signal processing circuitry of imaging sub-system 118 converts analog electrical signals to digital signals, it can transmit the digital signals to a data processing system to produce digital images such as fluorescence images 140. For example, the data processing system can perform various digital signal processing (DSP) algorithms (e.g., compression) for high-speed data processing. In some embodiments, at least part of the data processing system can be integrated with the signal processing circuitry on a same semiconductor die or chip. In some embodiments, at least part of the data processing system can be implemented separately from the signal processing circuitry (e.g., using a separate DSP chip or cloud computing resources). Thus, data can be processed and shared efficiently to improve the performance of the sample analytical system 110. It is appreciated that at least a portion of the signal processing circuitry and data processing system in imaging sub-system 118 can be implemented using, for example, CMOS-based application specific integrated circuits (ASIC), field programmable gate array (FPGA), discrete IC technologies, and/or any other desired circuit techniques.

It is further appreciated that power sub-system 122, optical sub-system 120, imaging sub-system 118, sensor(s) 116, control sub-system 114, and fluidic sub-system 112 may be separate systems or components or may be integrated with one another. The combination of at least a portion of optical sub-system 120, imaging sub-system 118, and sensors 116 is sometimes also referred to as a liquid photonic system.

Referencing FIG. 1, analytical system 110 provides fluorescence images 140 and/or other data to a computing device 103 to perform further processes including image preprocessing, cluster detection, feature extraction, and basecalling. Instructions for implementing one or more deep learning neural networks 102 reside on computing device 103 in computer program product 104 which is stored in storage 105 and those instructions are executable by processor 106. One or more deep learning neural networks 102 can be used for performing various processes described below. When processor 106 is executing the instructions of computer program product 104, the instructions, or a portion thereof, are typically loaded into working memory 109 from which the instructions are readily accessed by processor 106. In one embodiment, computer program product 104 is stored in storage 105 or another non-transitory computer readable medium (which may include being distributed across media on different devices and different locations). In alternative embodiments, the storage medium is transitory.

In one embodiment, processor 106 in fact comprises multiple processors which may comprise additional working memories (additional processors and memories not individually illustrated) including a graphics processing unit (GPU) comprising at least thousands of arithmetic logic units supporting parallel computations on a large scale. Other embodiments comprise one or more specialized processing units comprising systolic arrays and/or other hardware arrangements that support efficient parallel processing. In some embodiments, such specialized hardware works in conjunction with a CPU and/or GPU to carry out the various processing described herein. In some embodiments, such specialized hardware comprises application specific integrated circuits and the like (which may refer to a portion of an integrated circuit that is application-specific), field programmable gate arrays and the like, or combinations thereof. In some embodiments, however, a processor such as processor 106 may be implemented as one or more general purpose processors (preferably having multiple cores) without necessarily departing from the spirit and scope of the present invention.

User device 107 incudes a display 108 for displaying results of processing carried out by the one or more deep learning neural networks 102. In alternative embodiments, a neural network such as neural network 102, or a portion of it, may be stored in storage devices and executed by one or more processors residing on analytical system 110 and/or user device 107. Such alternatives do not depart from the scope of the invention.

Sequencing-by-Synthesis

FIG. 2 illustrates an exemplary sequencing-by-synthesis process 200 using an analytical system (e.g., system 110) in accordance with an embodiment of the present invention. In step 1 of process 200, the analytical system heats up a biological sample to break apart the two strands of a DNA molecule. One of the single strands will be used as the DNA template strand. FIG. 2 illustrates such a DNA template strand 202, which can be a genomic DNA. Template strand 202 may be a strand that includes a sequence of nucleotide bases (e.g., a long sequence having few hundreds or thousands of bases). It is understood that there may be many such templated strands generated from using the polymerase chain reaction (PCR) techniques. It is further understood that there may also be other isolation and purification processes applied to the biological sample to obtain the DNA template strands.

In step 2 of process 200, the analytical system generates many DNA fragments from the DNA template strand 202. These DNA fragments, such as fragments 204A-D shown in FIG. 2, are smaller pieces containing fewer number of nucleotide bases. These DNA fragments can thus be sequenced in a massively parallel manner to increase the throughput of the sequencing process. Step 3 of process 200 performs adapter ligation. Adapters are oligonucleotides with sequences that are complementary to the priming oligos disposed on the flowcell(s). The ends of the nucleic acid fragments are ligated with adapters to obtain ligated DNA fragments (e.g., 206A-D) to enable the subsequent sequencing process.

The DNA fragmentation and adapter ligation steps prepare the nucleic acids to be sequenced. These prepared, ready-to-sequence samples are referred to as "libraries" because they represent a collection of molecules that are sequenceable. After the DNA fragmentation and adapter ligation steps, the analytical system generates a sequencing library representing a collection of DNA fragments with adapters attached to their ends. In some embodiments, prepared libraries are also quantified (and normalized if needed) so that an optimal concentration of molecules to be sequenced is loaded to the system. In some embodiments, other processes may also be performed in the library preparation process. Such processes may include size selection, library amplification by PCR, and/or target enrichment.

After library preparation, process 200 proceeds to step 4 for clonal amplification to generate clusters of DNA fragment strands (also referred to as template strands). In this step, each of the DNA fragments is amplified or cloned to generate thousands of identical copies. These copies form clusters so that fluorescent signals of the clusters in the subsequent sequencing reaction are strong enough to be detected by the analytical system. One such amplification process is known as bridge amplification. In a bridge amplification process, a tile (e.g., tile 208 in FIG. 2) is used and priming oligos are disposed on the tile. Each DNA fragment in the library anneals to the primer oligo disposed on the tile via the adapters attached to the DNA fragment. The complementary strand of a ligated DNA fragment is then synthesized. The complementary strand folds over and anneals with the other type of primer oligo disposed on the tile. A double-stranded bridge is thus formed after synthesis of the complementary strand.

The double-stranded bridge is denatured, forming two single strands attached to the tile. This process of bridge amplification repeats many times. The double-stranded clonal bridges are denatured, the reverse strands are removed, and the forward strands remain as clusters for subsequent sequencing. Two such clusters of strands are shown as clusters 214 and 216 in FIG. 2. Many clusters having different DNA fragments can be attached to a tile. For example, cluster 214 may be a cluster of ligated fragmented DNA 206A disposed on tile 208; and cluster 216 may be a cluster of ligated fragmented DNA 206B also disposed on tile 208. The subsequent sequencing can be performed in parallel to some or all of these different clusters disposed on a tile and in turn, some or all the clusters disposed on many tiles of the flowcell(s). The sequencing process can thus be massively parallel.

Referencing FIG. 2, after the clonal amplification in step 4, process 200 proceeds to step 5, where the clusters are sequenced by synthesis (SBS). In this SBS step, nucleotides are incorporated by a DNA polymerase into the complementary DNA strands of the clonal clusters of the DNA fragments one base at a time in each synthesis cycle. For example, as shown in FIG. 2, if cycle 1 is a beginning cycle, a first complementary nucleotide base is incorporated to the complementary DNA strand of each strand in cluster 214. FIG. 2 only shows one strand in cluster 214 for simplicity. But it is understood that similar processes can occur to some or all other strands of cluster 214, some or all other clusters on tile 208, some or all other tiles, and some or all other flowcells. This synthesis process repeats in cycle 2, where a second complementary nucleotide base is incorporated to the complementary DNA strand. This synthesis process then repeats in cycles 3, 4, and so on, until complementary nucleotide bases are incorporated for all bases in the template strand 206A or until a predetermined number of cycles is reached. Thus, if the template strand 206A has "n" nucleotide bases, there may be "n" cycles or a predetermined number of cycles (less than "n") for the entire sequencing-by-synthesis process. The complementary strand 207A is at least partially completed after all the synthesis cycles. In some embodiments, this synthesis process can be performed for some or all strands, clusters, tiles, and flowcells in parallel.

Step 6 of process 200 is an imaging step that can be performed after step 5 or in parallel with step 5. As one example, a flowcell can be imaged after the sequencing-by-synthesis process is completed for the flowcell. As another example, a flowcell can be imaged while the sequencing-by-synthesis process is being performed on another flowcell, thereby increasing the throughput. Referencing FIG. 2, in each cycle, the analytical system captures one or more images of the tile (e.g., images 228A-D) of a flowcell. The images represent the fluorescent signals detected in the particular cycle for all the clusters disposed on the tile. In some embodiments, the analytical system can have a four-channel configuration, where four different fluorescent dyes are used for identifying the four nucleotide bases. For example, the four fluorescence channels use different types of dyes for generating fluorescent signals having different spectral wavelengths. Different dyes may each bind with a different target and produce signals with a different fluorescence color or spectrum. Examples of the different dyes may include a Carboxyfluorescein (FAM) based dye that produces signals having a blue fluorescence color, a Hexachloro-fluorescein (HEX) based dye that produces signals having a green fluorescence color, a 6-carboxy-X-rhodamine (ROX) based dye that produces signals having a red fluorescence color, a Tetramethylrhodamine (TAMRA) based dye that produces signals having a yellow fluorescence color.

In a four-channel configuration, the analytical system captures an image of the same tile for each channel. Therefore, for each tile, the analytical system produces four images in each cycle. This imaging process can be performed with respect to some or all the tiles and flowcells, producing a massive number of images in each cycle. These images represent the fluorescent signals detected in that particular cycle for all the clusters disposed on the tile. The images captured for all cycles can be used for basecalling to determine the sequences of the DNA fragments. A sequence of an DNA fragment includes an ordered combination of nucleotide bases having four different types, i.e., Adenine (A), Thymine (T), Cytosine (C), and Guanine (G). The sequences of multiple DNA fragments can be integrated or combined to generate the sequence of the original genomic DNA strand. Embodiments of this invention described below can process the massive numbers of images in an efficient way and perform basecalling using improved architectures of deep learning neural networks. The basecalling process according to the embodiments of this invention thus has a faster speed and a lower error rate. While the above descriptions use DNA as an example, it is understood that the same or similar processes can be used for other nucleic acid, such as RNA and artificial nucleic acid.

Figure 3:
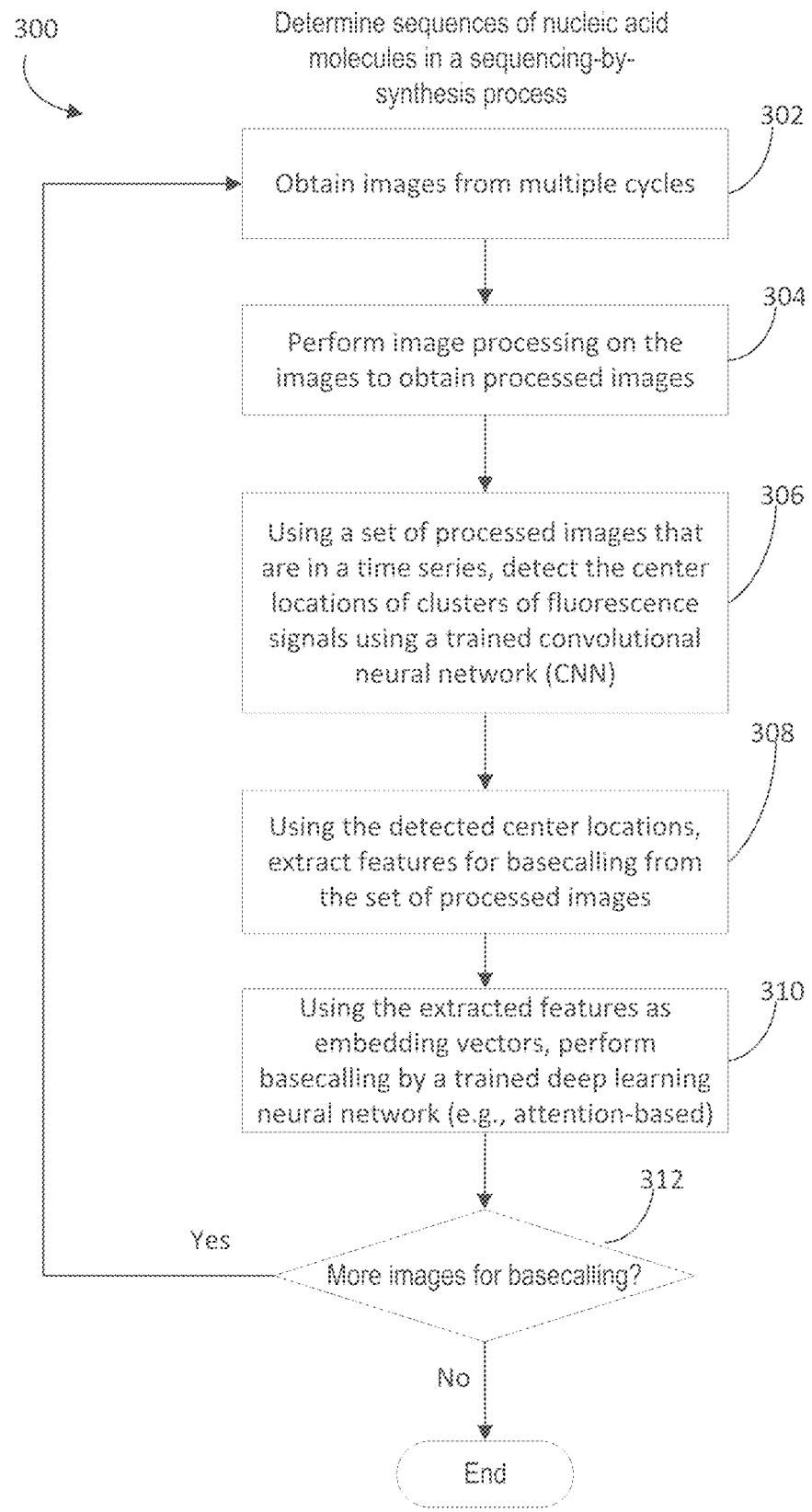
FIG. 3 is a flowchart illustrating a method for determining sequences of nucleic acid molecules in a sequencing-by-synthesis process in accordance with an embodiment of the present invention.

FIG. 3 is a flowchart illustrating a method 300 for determining sequences of nucleic acid molecules in a sequencing-by-synthesis process in accordance with an embodiment of the present invention. Method 300 can be performed by a computing device 103 as shown in FIG. 1. Step 302 of method 300 obtains images of fluorescent signals captured by the analytical system in a plurality of synthesis cycles (e.g., images 228A-D captured in cycles 1-4 shown in FIG. 2). As described above, these images of fluorescent signals may be captured in a plurality of different fluorescence channels of the analytical system. Step 304 of method 300 preprocesses these images of fluorescent signals to obtain processed images. A set of the preprocessed images that are in a time series is selected. Based on the selected set of the processed images, step 306 detects center positions of clusters of the fluorescent signals using a trained convolutional neural network (CNN). Step 308 extracts, based on the center positions of the clusters of fluorescent signals, features from the set of the processed images to generate feature embedding vectors. Using the feature embedding vectors, step 310 performs basecalling by a trained attention-based neural network (e.g., a Transformer deep learning neural network). Step 312 determines if there are more images to be processed for basecalling. If the answer is "yes", the process repeats from step 302. If the answer is "no", the process ends. Steps 304, 306, 308, and 310 of method 300 are described in greater detail below.

Image Preprocessing

Figure 4:
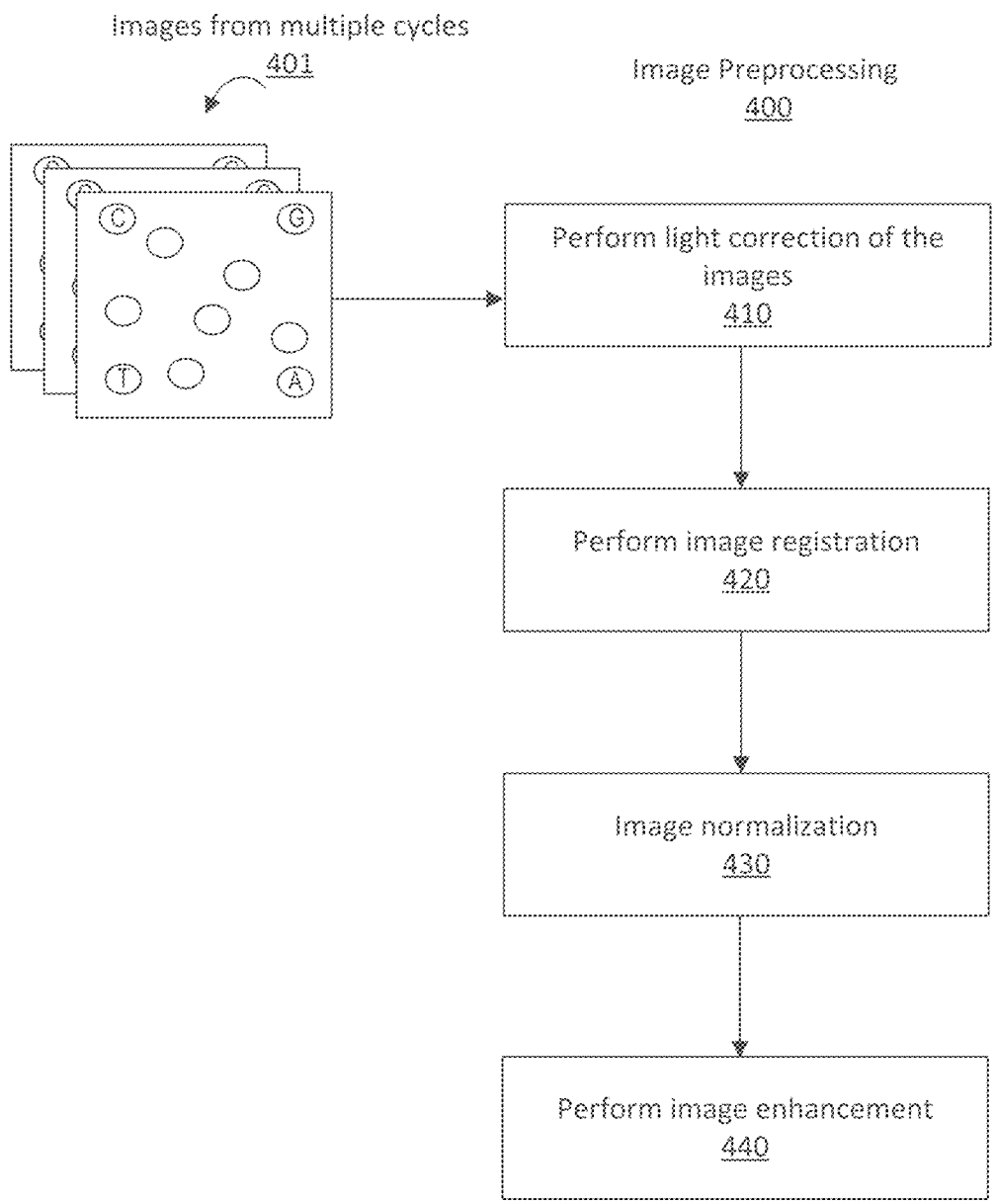
FIG. 4 is a flowchart illustrating a method of image preprocessing in accordance with an embodiment of the present invention.

FIG. 4 is a flowchart illustrating a method 400 for image preprocessing in accordance with an embodiment of the present invention. Method 400 can be used to implement step 304 of method 300. Method 400 is used to preprocess images of fluorescent signals captured by the analytical system in multiple synthesis cycles. In FIG. 4, images 401 represent those images that are to be processed. Images 401 may include, for example, images 228A-D captured in cycles 1-4 shown in FIG. 2. Processing the images before performing the subsequent steps of cluster detection and the basecalling processes improves the accuracy of cluster detection, reduces signal interference between close-by clusters, and improves the accuracy of basecalling.

As shown in FIG. 4, in some embodiments, step 410 of method 400 performs light correction of the images 401. Due to various environmental and equipment conditions, one or more of images 401 captured by an analytical system may be overly bright, overly dark, having unbalanced brightness and contrast, having uneven light exposure, or other undesired light conditions. These light conditions of the images may affect the subsequent cluster detection and basecalling processes and therefore need to be corrected or at least mitigated.

In step 410, a light correction process can be performed by using, for example, a Gamma correction, a homomorphic filtering, etc. Gamma correction is a nonlinear operation used to encode and decode luminance or tristimulus values of an image or video. It can be used to increase or decrease the brightness, contrast, etc. of an image. Homomorphic filtering is a technique where an image is processed to generate a nonlinear mapping to a different domain in which linear filter techniques are applied, followed by mapping back to the original domain. Homomorphic filter simultaneously normalizes the brightness across an image and increases contrast. Homomorphic filtering can be used to remove multiplicative noise. It is understood that other light correction techniques can also be used in step 410.

Figure 5:
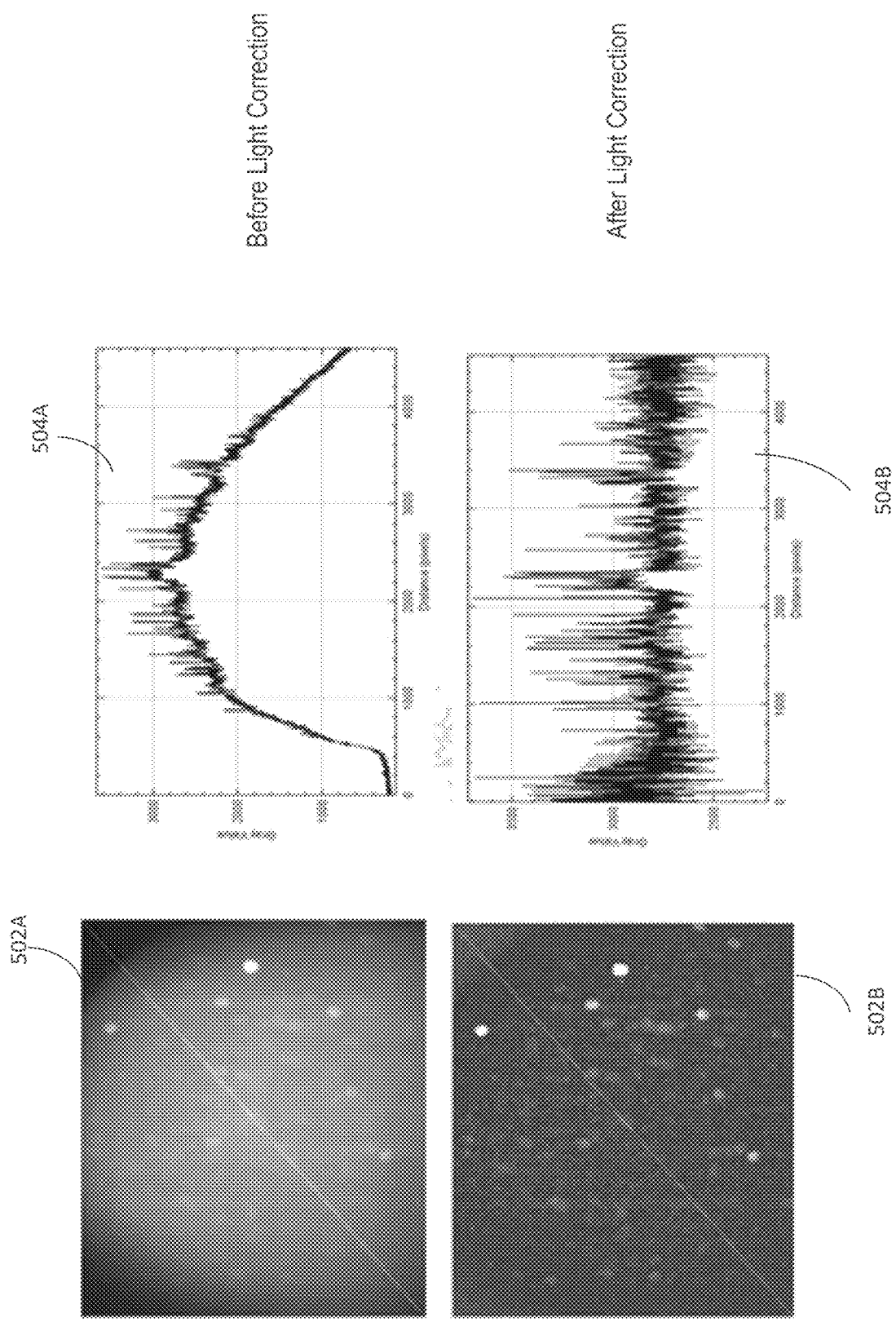
FIG. 5 compares fluorescence images and signal distributions obtained before performing a light correction process and after performing a light correction process in accordance with an embodiment of the present invention.

FIG. 5 compares fluorescence images 502A and 502B and their respective signal distributions 504A and 504B before performing a light correction process and after performing a light correct process. As shown in FIG. 5, before light correction, image 502A may be overly bright in the center of the image and/or having a low contrast, which may render cluster detection difficult or inaccurate. Image 502B is obtained after light correction is performed on image 502A. The brightness and contrast of image 502A has been improved such that the clusters are more detectable. The distributions of 504A and 504B reflect the uneven brightness distribution before light correction and more constant brightness distribution after light correction.

Referencing back to FIG. 4, step 420 of method 400 performs image registration using the images 401 from multiple cycles. Image registration is a process of aligning different sets of data such that they can be compared, measured, and/or integrated using one coordinate system. These data may include multiple images captured in different synthesis cycles using one fluorescence channel, multiple images captured in a same synthesis cycle using different fluorescence channels, images captured by different sensors, images captured at different times or viewpoints, etc. As described above, for example, an analytical system (e.g., system 110) may be configured to have four fluorescence channels. Thus, for a particular synthesis cycle, the analytical system captures four images of a same tile corresponding to the four different fluorescence channels. The four images are captured using four different image sensors (e.g., cameras) to detect signals having four respective fluorescence wavelengths.

In some embodiments of the imaging process, the analytical system moves the stage supporting the flowcell such that the particular tile being imaged is positioned underneath the different image sensors one at a time. The four images in each cycle are then captured by these different fluorescence image sensors for the same tile. The same process then repeats for the next tile of the flowcell. After a predetermined number of tiles or all tiles of the flowcell are imaged, the analytical system proceeds to capture images for the next synthesis cycle. The re-positioning of the tile between cycles are not entirely accurate because the stage movements of the flowcell may have re-positioning errors. For example, the images between cycles may be several pixels out of alignment. Thus, the image registration process is performed to align the images captured across different synthesis cycles to compensate for the re-positioning error. Moreover, within the same cycle, images are captured by different image sensors across different fluorescence channels. These images may also not be in alignment due to stage movements and/or misalignment of optical paths between channels. The image registration process can thus also be performed to align images captured across different fluorescence channels.

Figure 6:
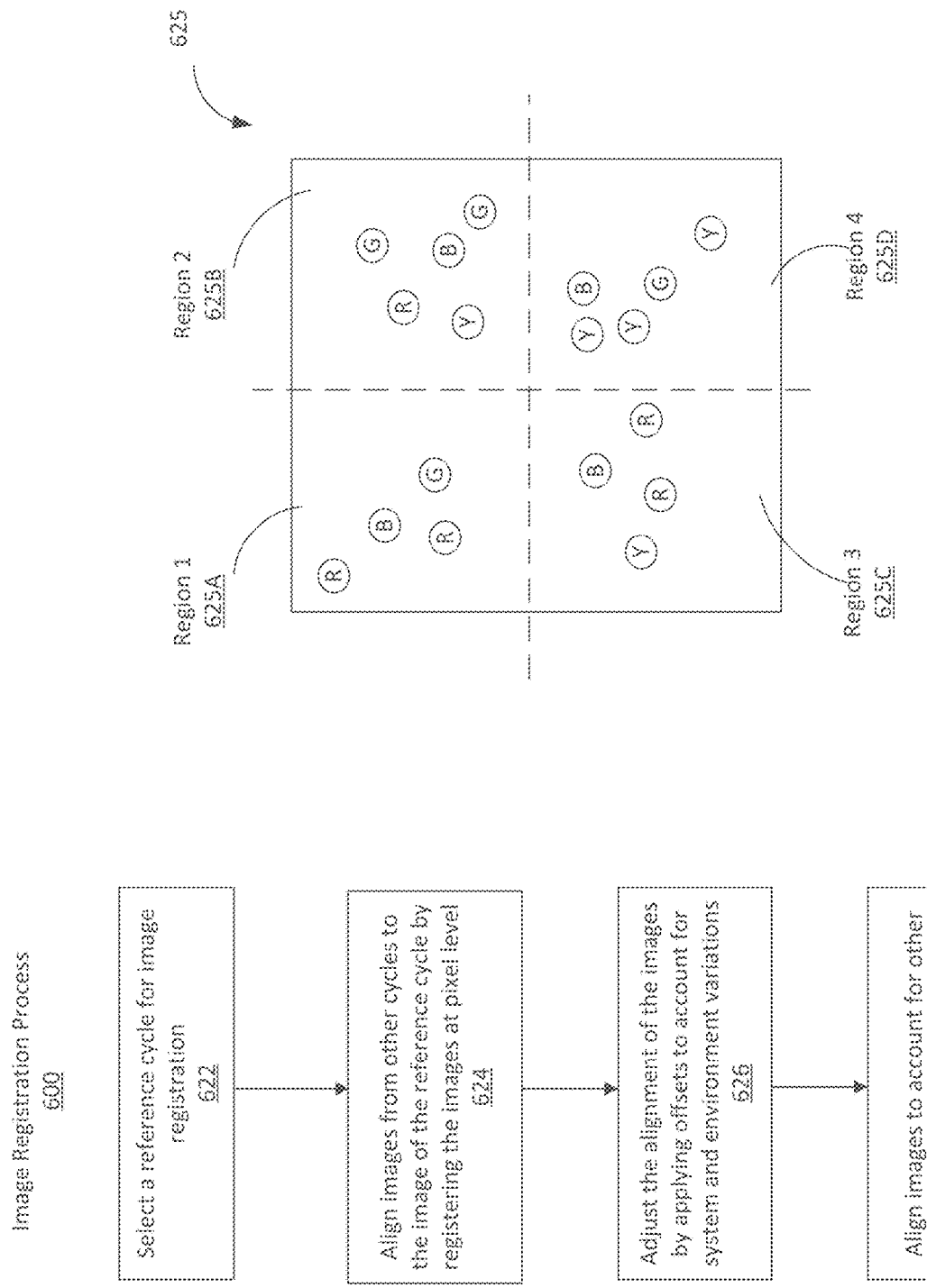
FIG. 6 is a flowchart illustrating a method of image registration in accordance with an embodiment of the present invention.

FIG. 6 is a flowchart illustrating a method 600 of image registration in accordance with an embodiment of the present invention. Method 600 can be used to implement step 420 of method 400. Referencing FIG. 6, step 622 of method 600 selects a reference synthesis cycle for image registration. The reference synthesis cycle can be any cycle but is typically the first cycle or the beginning cycle. The image captured in the reference synthesis cycle serves as a reference image to which images captured in the other synthesis cycles are aligned. Step 624 aligns images from other synthesis cycles to the image of the reference cycle. For example, the alignment can be performed by applying an image registration algorithm at the pixel level. The image registration algorithm can be an intensity-based algorithm or a feature-based algorithm. The intensity-based algorithm compares the intensity patterns in images via correlation metrics and the feature-based algorithm finds image correspondence using image features such as points, lines, and contours. The image registration can also be performed using algorithms such as correlation-based registration, mutual information registration, linear transformation, phase correlation, cross-correlation, sum of squared intensity differences, ratio image uniformity, etc. It is understood that any other type of registration algorithms may also be used to align the images from different cycles to the image of the reference cycle.

In some embodiments, the alignment of the images across multiple cycles may need to be adjusted to account for certain conditions and variations such as incorrect focusing of the image sensors, warping of the flowcell caused by temperature variations, etc. Therefore, step 626 of method 600 performs such adjustments by applying offsets to account for system variations and/or environmental variations. In some embodiments, the offsets can be calculated and applied to a sub-region of an image, rather than the entire image. Image 625 is an exemplary fluorescence image of a tile. Image 625 may have multiple clusters of fluorescent signals having different colors (illustrated by circles with "R", "B", "G", "Y" representing difference colors red, blue, green, and yellow, respectively). The different colors (e.g., red, blue, green, and yellow) represent different clusters of fluorescent signals having different wavelengths. Suppose image 625 shown in FIG. 6 is an image that has been aligned to the image of the reference cycle (e.g., by using cross-cycle registration), adjustments of the alignment can be calculated and applied to different regions of image 625. In one example, image 625 is divided to four regions 625A-D. For each region, a same or different offset is calculated and applied independently to account for system and/or environmental variations affecting the individual region. It is understood that an image can be divided to any number of regions. Adjustments of the alignments can thus be performed to any number of regions independently from other regions.

Step 628 of method 600 aligns images to account for other possible variations, such as cross-channel variations caused by cross-channel image shifting, image scaling, and/or image rotation.

With reference back to FIG. 4, method 400 can also include a step 430 for image normalization. Step 430 performs image normalization by, for example, adjusting signal intensity range or equalizing contrast between images. The image normalization process thus increases the signal-to-noise (SNR) ratio of the image, thereby further improving the image quality.

Figure 7:
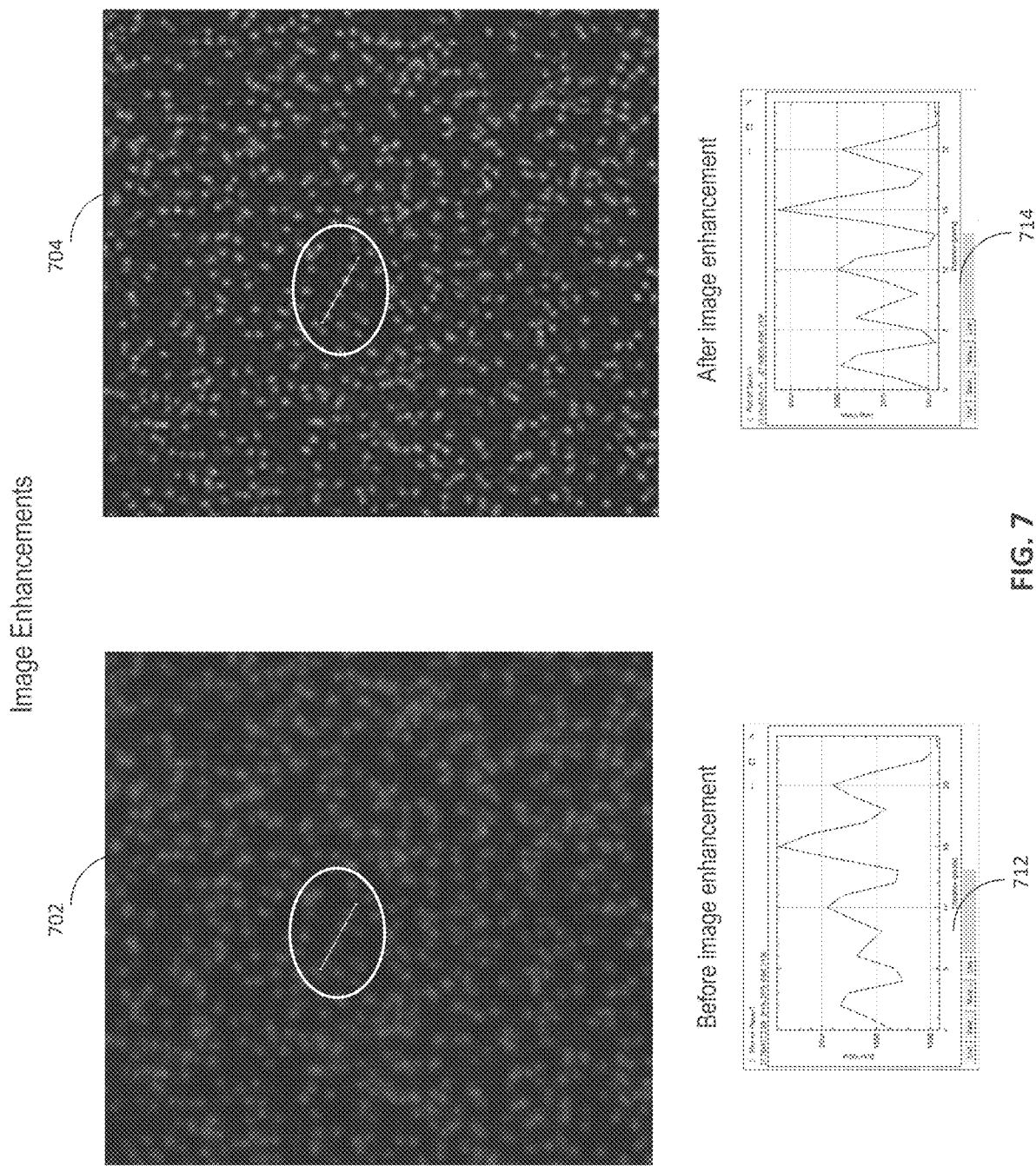
FIG. 7 compares fluorescence images and signal distributions obtained before performing an image enhancement process and after an image enhancement process in accordance with an embodiment of the present invention.

In some embodiments, method 400 also includes a step 440 for performing further image enhancement. Various image enhancement algorithms can be used in step 440. As one example, the Ricker wavelet based algorithm (also referred to as Mexican Hat wavelet) is used to smooth the center pixel of a cluster and to emphasize the edge of the cluster. The multidimensional generalization of the 2-dimensional Mexican Hat wavelet is referred to as a Laplacian of Gaussian function, which can also be applied to perform image enhancement. FIG. 7 illustrates a fluorescence image 702 obtained before image enhancement and a fluorescence image 704 obtained after image enhancement. As illustrated, after image enhancement, clusters of fluorescent signals are enhanced in one or more ways. For example, the clusters are shaper in contrast and/or sharper at edge areas of the clusters. Signal to noise ratios may be higher for at least some of the clusters. FIG. 7 further illustrates a waveform 712 representing the signal intensity distribution associated with a line in image 702. Similarly, waveform 714 represents the signal intensity distribution associated with a line in image 704. The two lines in images 702 and 704 are drawn across the same area for comparison. As shown in FIG. 7, in waveform 714, the neighboring peaks are more separatable and distinguishable than those in waveform 712. In other words, close-by clusters are more distinguishable after image enhancement than before.

It is understood that steps in method 400 can be added, removed, or reordered such that they are performed in any desired order. For example, one or more of steps 410, 420, 430, and 440 may not be necessary for some images (e.g., an image may not need light correction and thus step 410 may not be necessary) and thus can be removed for those images. Some of these steps may also not be needed depending on the equipment (e.g., if an analytical system has very small cross-channel interferences, part of step 420 for registration of cross-channel images may not be necessary). Further, one or more steps 410, 420, 430, and 440 may be performed in a different order or in parallel. For example, step 430 may be performed together with step 410 and before step 420.

Cluster Detection

Figure 8:
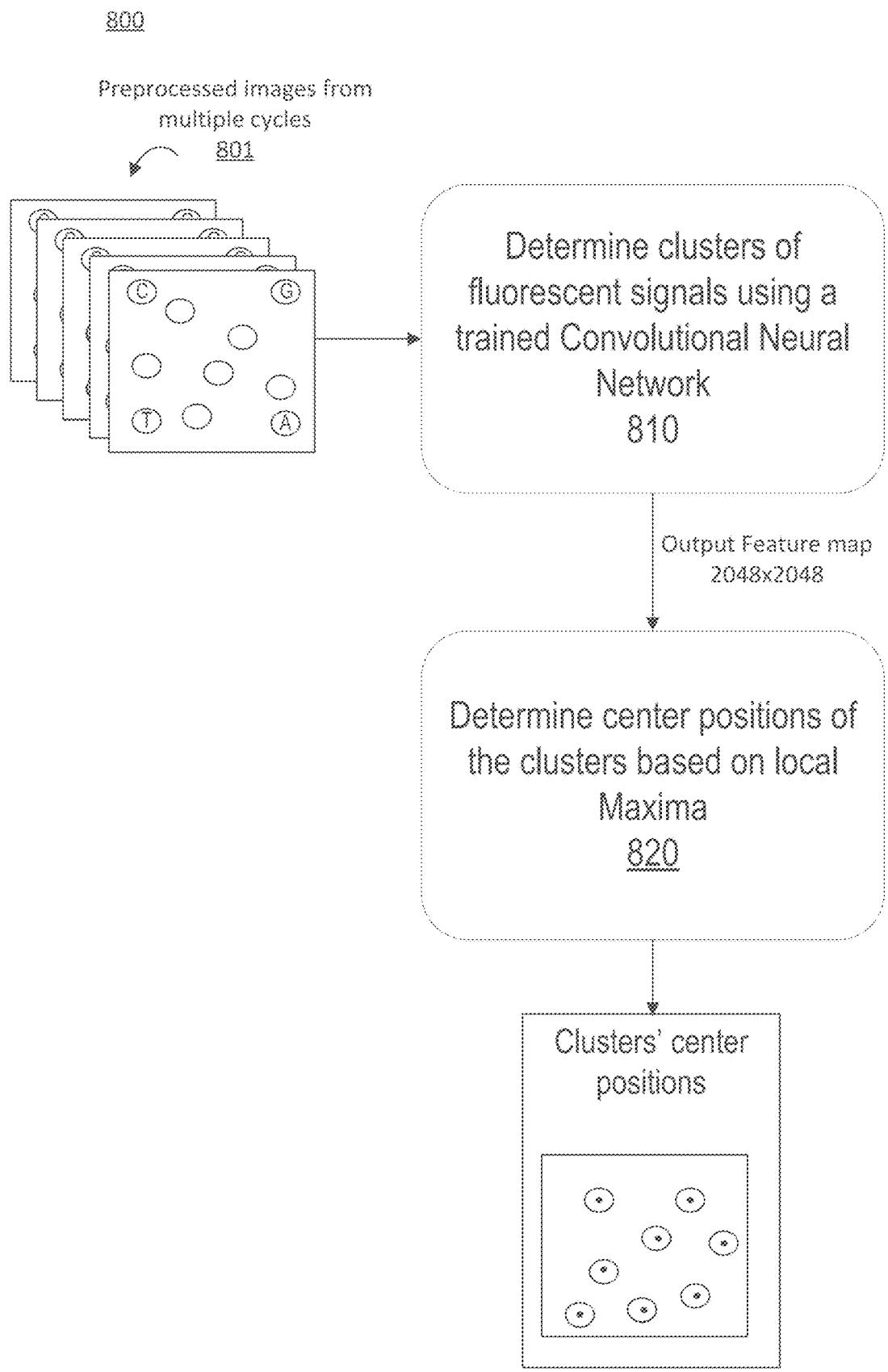
FIG. 8 is a flowchart illustrating a method for detecting center positions of clusters of fluorescent signals in accordance with an embodiment of the present invention.

A set of images that have been processed (e.g., using method 400) can be used to detect center positions of clusters of fluorescent signals (or simply cluster detection). FIG. 8 is a flowchart illustrating a method 800 for detecting center positions of clusters of fluorescent signals. Method 800 can be used to implement step 306 of method 300 in FIG. 3. Referencing FIG. 8, in some embodiments, a set of processed images 801 is selected from all processed images. The selected set of processed images 801 includes processed images obtained corresponding to multiple synthesis cycles. The synthesis cycles may or may not be consecutive. As one example, the set of processed images may include processed images using images captured in five consecutive synthesis cycles. Consecutive synthesis cycles are performed in a time serial manner. Four of such consecutive cycles are shown in FIG. 2 (e.g., cycles 1-4 shown in FIG. 2). As described above, in a four-channel configuration, the analytical system obtains four images in each cycle. Therefore, for a four-channel configuration, the set of processed images provided for cluster detection has total of 20 images corresponding to five consecutive synthesis cycles. It is understood that any number of cycles may be selected and therefore the set of processed images may have any number of images (e.g., if seven cycles are selected for processing, total of 28 images would be selected). In some embodiments, images from cycles that are not consecutive may be selected (e.g., using every other cycles or any desired cycles). In some embodiments, all processed images may be selected for cluster detection.

As described above, a fluorescence image of a tile represents fluorescent signals corresponding to clusters of the DNA fragments disposed on the tile. Therefore, the fluorescent signals also form clusters. Each of the clusters of fluorescent signals corresponds to a nucleotide base A, T, C, or G. For determining the probabilities of basecalling and in turn determining whether a cluster of fluorescent signals corresponds to a particular nucleotide base, the center positions of these clusters of fluorescence need to be determined. Method 800 first finds the clusters of fluorescent signals using a trained convolutional neural network (CNN) in step 810. Step 810 generates an output feature map. Using the output feature map, the center positions of the clusters are determined using a local Maxima algorithm in step 820.

Figure 9:
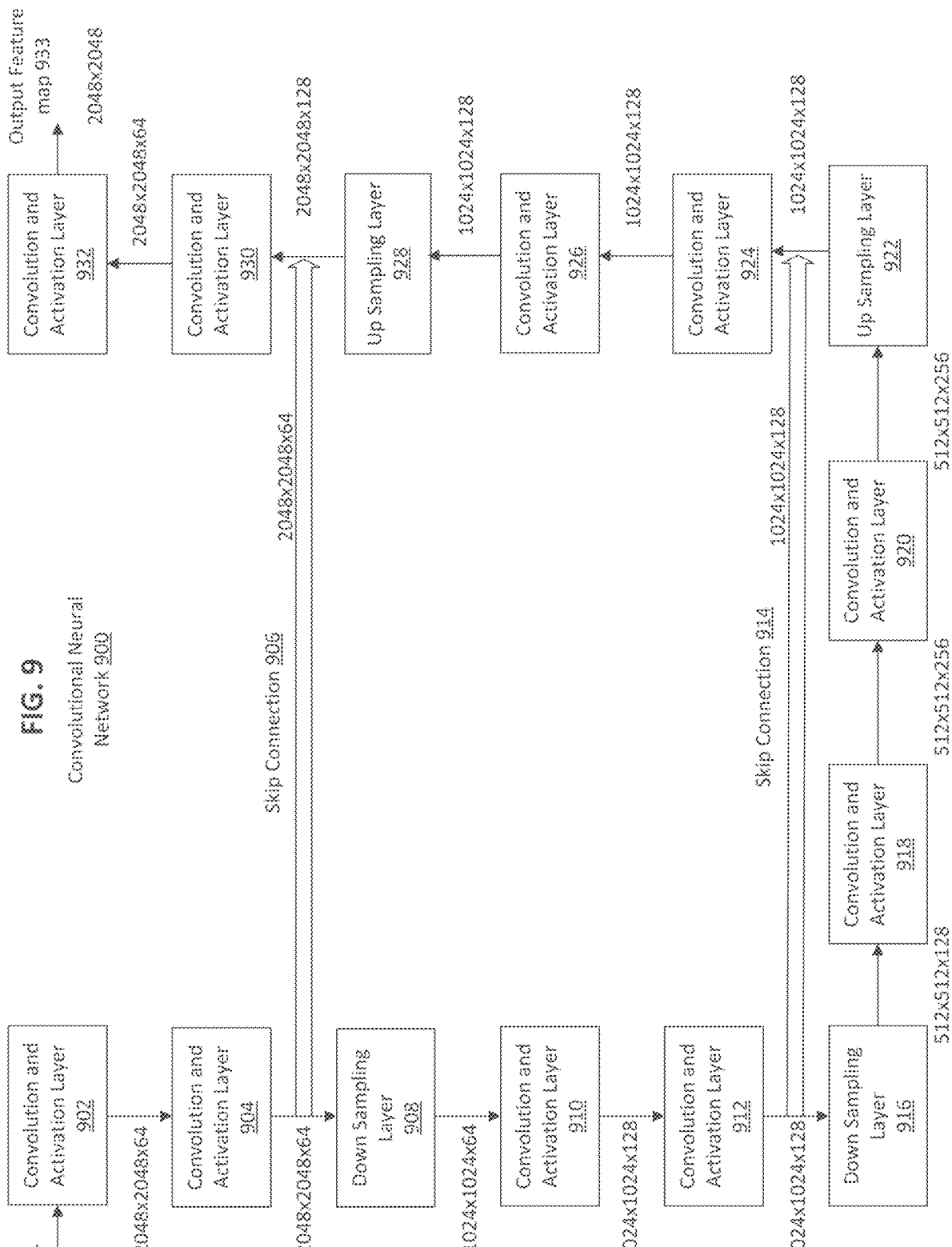
FIG. 9 is a block diagram illustrating an exemplary Convolutional Neural Network (CNN) for detecting center positions of clusters of fluorescent signals in accordance with an embodiment of the present invention.

FIG. 9 is a block diagram illustrating an exemplary convolutional neural network (CNN) 900 for detecting the clusters of fluorescent signals using a selected set of processed images 901. As described above, a selected set of processed images includes processed images corresponding to multiple synthesis cycles (e.g., total of 20 images obtained corresponding to five consecutive cycles for a four-fluorescence channel configuration). In some embodiments, each one of these processed images has a resolution of 2048 pixels×2048 pixels (height×width). And therefore, for total of 20 images, the input data is an array having dimensions of 2048×2048×20 (i.e., height×width×number of images). In the above example, the first and second dimensions of the input array are represented by pixels and the third dimension is represented by the number of images. The third dimension of the input array (and other such arrays) is also referred to as a channel. That is, the input array 901 is considered to have 20 channels in the above example. The number of channels (i.e., the value of the third dimension) may be changed after the input array passes through the CNN 900.

As shown in FIG. 9, the input array 901 is provided to a trained CNN 900. CNN 900 generally includes an input layer, one or more hidden layers, and an output layer. The input layer receives the input array and the output layer produces the output feature map. Any layers between the input layer and the output layer may be referred to as hidden layers. Using one or more of the input layer, the hidden layers, and the output layer, CNN 900 can perform various mathematical operations including convolution, down sampling, up sampling, and skip connection.

As shown in FIG. 9, in one embodiment, CNN 900 includes multiple convolution and activation layers 902, 904, 910, 912, 918, 920, 924, 926, 930, and 932. A convolution and activation layer may be two separate layers performing two convolution and activation operations separately or a combined layer performing both operations. A convolution operation uses multiple convolution kernels to slide on each image of the input array and performs multiplication and addition operations to generate a new array (also referred to as features or a feature map). A convolution kernel is a kind of matrix, the dimensions of which can be configured by using a parameter. For example, the dimensions of the kernel can be configured to be 3×3. The specific values of the elements in the convolution kernel are configurable and continuously updated during a network training process. The training process of a CNN 900 iteratively updates the values of the kernels and a bias to make the output data of the CNN 900 and the known or predicted output data (also referred to as the labelled data) as close as possible.

The dimensions of the output features of a convolution operation can be controlled by configuring the hyperparameters of the convolution operation (such as the size of the convolution kernel, the number of convolution kernels, filling, and the sliding step size). In a parameter configuration, a convolution operation may only change the number of channels of the input array without changing the image size. For example, in FIG. 9, the input array of convolution and activation layer 902 has dimensions of 2048×2048×20 and its output feature map has dimensions of 2048×2048×64. That is, when layer 902 performs the convolution operation, the resolution of each channel (i.e., the third dimension) stays the same, but the number of channels changes from 20 to 64.

An activation operation applies a non-linear activation function to each element of the input array. The activation function introduces non-linearity into the output of a neuron. It helps to decide if a neuron would fire or not. An activation function can be, for example, a Rectified Linear Unit (ReLU) function, a SoftMax function, a Sigmoid function, a tan h function, a Leaky ReLU function, etc. The output features of a convolution and activation layer are then passed to the next layer.

The down sampling layer performs a down sampling operation to reduce the size of the features. FIG. 9 shows such down sampling layers 908 and 916. For example, down sampling layer 908 reduces the dimensions of its input features from 2048×2048×64 to 1024×1024×64. The down sampling operation can be achieved by retaining the average (also referred to as average pooling) or maximum (also referred to as max pooling) value of the elements in a certain range (e.g., in a 2×2 window area). The down sampling operation may be a non-linear down-sampling. For example, the max pooling partitions the input image or feature map into a set of rectangles and for each such rectangle, outputs the maximum value. The down sampling operation reduces the computations in the next layer by reducing the dimensions of its output feature map.

The up-sampling layer performs an up-sampling operation to increase the dimensions of the feature map by interpolation. FIG. 9 shows such up-sampling layers 922 and 928. For example, up sampling layer 922 increase the dimensions of its input features from 512×512×256 to 1024×1024×128. An up-sampling operation may use various types of interpolation algorithms, such as zero padding, piece-wise linear interpolation, piece-wise constant interpolation, piece-wise cubic spline interpolation, etc.

As shown in FIG. 9, CNN 900 also includes one or more skip connections 906 and 914 configured to perform skip connection operations. A skip connection operation facilitates concatenating of the output feature maps of different steps in the channel dimension. The skip connection operation concatenates the features at the two ends of the skip connection. For example, as shown in FIG. 9, skip connection 914 copies the features at its left end (i.e., the features having dimensions of 1024×1024×128 at the output of convolution and activation layer 912) to its right end (i.e., at the input of convolution and activation layer 924). The copied features are then concatenated to the output features of up sampling layer 922 (i.e., the features having a dimension of 1024×1024×128) to obtain features having dimensions of 1024×1024×256. The concatenated features are used as the input array to convolution and activation layer 924.

Using the convolution and activation layers, down sampling layers, up-sampling layers, and skip connections, the trained CNN 900 takes a set of processed images as input array 901 and produces an output feature map 933 corresponding to clusters of fluorescent signals represented in the set of processed images. The set of processed images used as input array 901 may be a subset of all processed images or all processed images. In the example shown in FIG. 9, the input array 901 has dimensions of 2048×2048×20 and the output feature map 933 has dimensions of 2048×2048. The output feature map 933 of CNN 900 captures the result of applying the convolution kernels to the input array 901 of the processed images. The output feature map 933 of CNN 900 thus includes features representing the clusters of fluorescent signals represented in the entire selected set of processed images in the input array 901. Compared to input array 901, output feature map 933 has significantly reduced dimensions (e.g., the third dimension or channel is reduced), which is used for subsequent feature extraction and basecalling processes. Using CNN 900, the processes of cluster detection and basecalling can have a faster detection speed and can generate more robustness and accuracy result. It is understood that FIG. 9 illustrates a CNN 900 with exemplary layer configurations. Other configurations are also possible. For example, more or fewer convolution layers, activation layers, up-sampling layers, down sampling layers, and skip connections may be used in CNN 900 without significantly impacting the performance of the network. Further, the order of the layers may also be configured in any desired manner.

In the output feature map 933 produced by CNN 900, the intensity of each pixel represents the probability that this pixel belongs to a cluster of fluorescent signals. By training the CNN 900 as described above, the intensities of the pixels in the overlapping area of neighboring clusters are smaller than the areas that are closer to the center of the neighboring clusters. Therefore, the output feature map 933 produced by CNN 900 separates the clusters of fluorescent signals from one another. This output feature map 933 enhances the accuracy and robustness of identifying individual clusters.

Referencing back to FIG. 8, using the output feature map obtained from CNN 900 (e.g., output feature map 933 having dimensions of 2048×2048), step 820 of method 800 determines the center positions of the clusters of fluorescent signals. In one embodiment, a local maximum search algorithm is applied to this feature map to determine the cluster center positions. A local maximum search algorithm finds a maximum signal value (e.g., the largest intensity or the highest probability) within a local or neighborhood area of a map. As the feature map represents multiple clusters, multiple center locations of the clusters can be determined using the local maximum search algorithm. The local maximum search algorithm results in a more accurate determination of the clusters' center positions.

Figure 10:
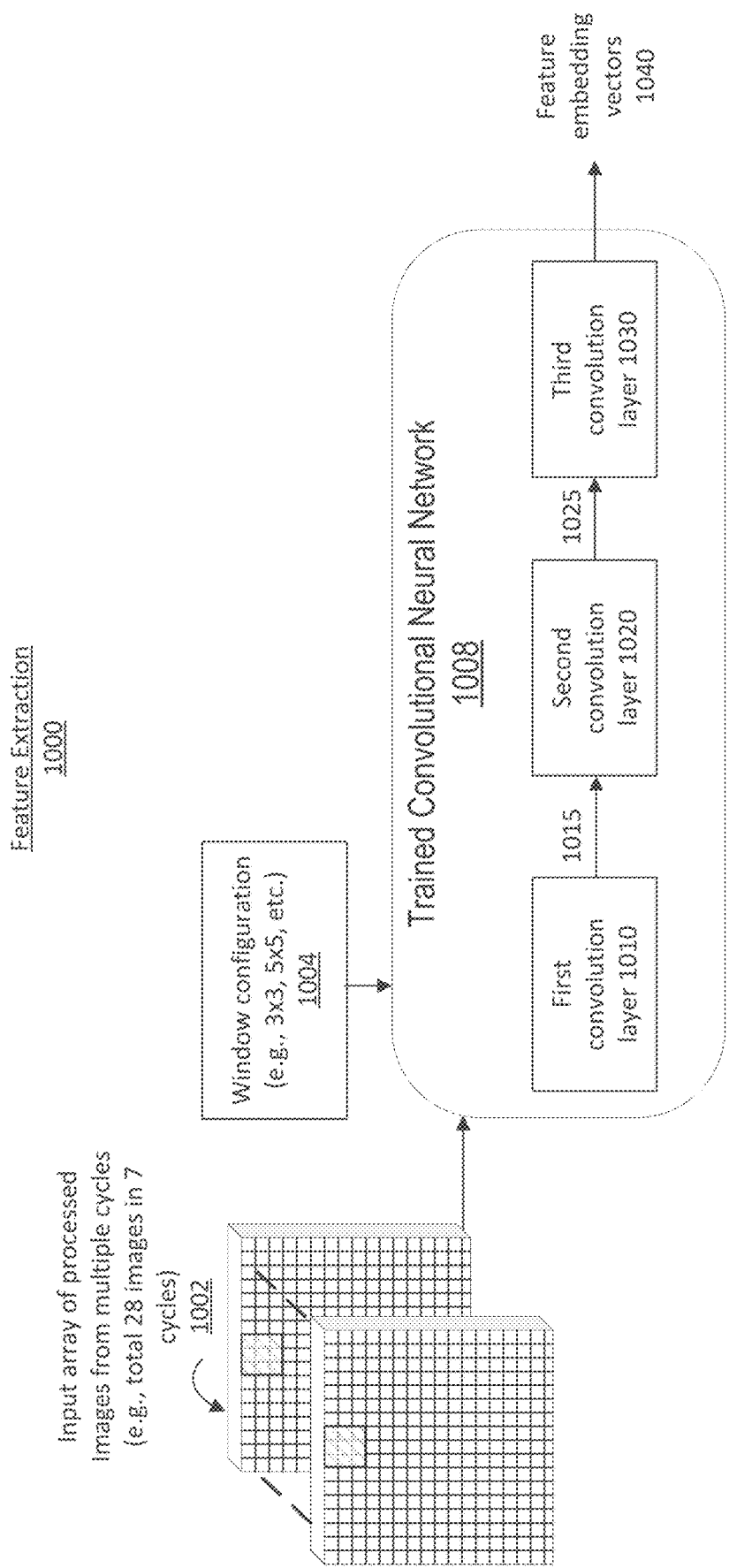
FIG. 10 is a block diagram illustrating a process of feature extraction using another CNN in accordance with one embodiment of the present invention.
Figure 11:
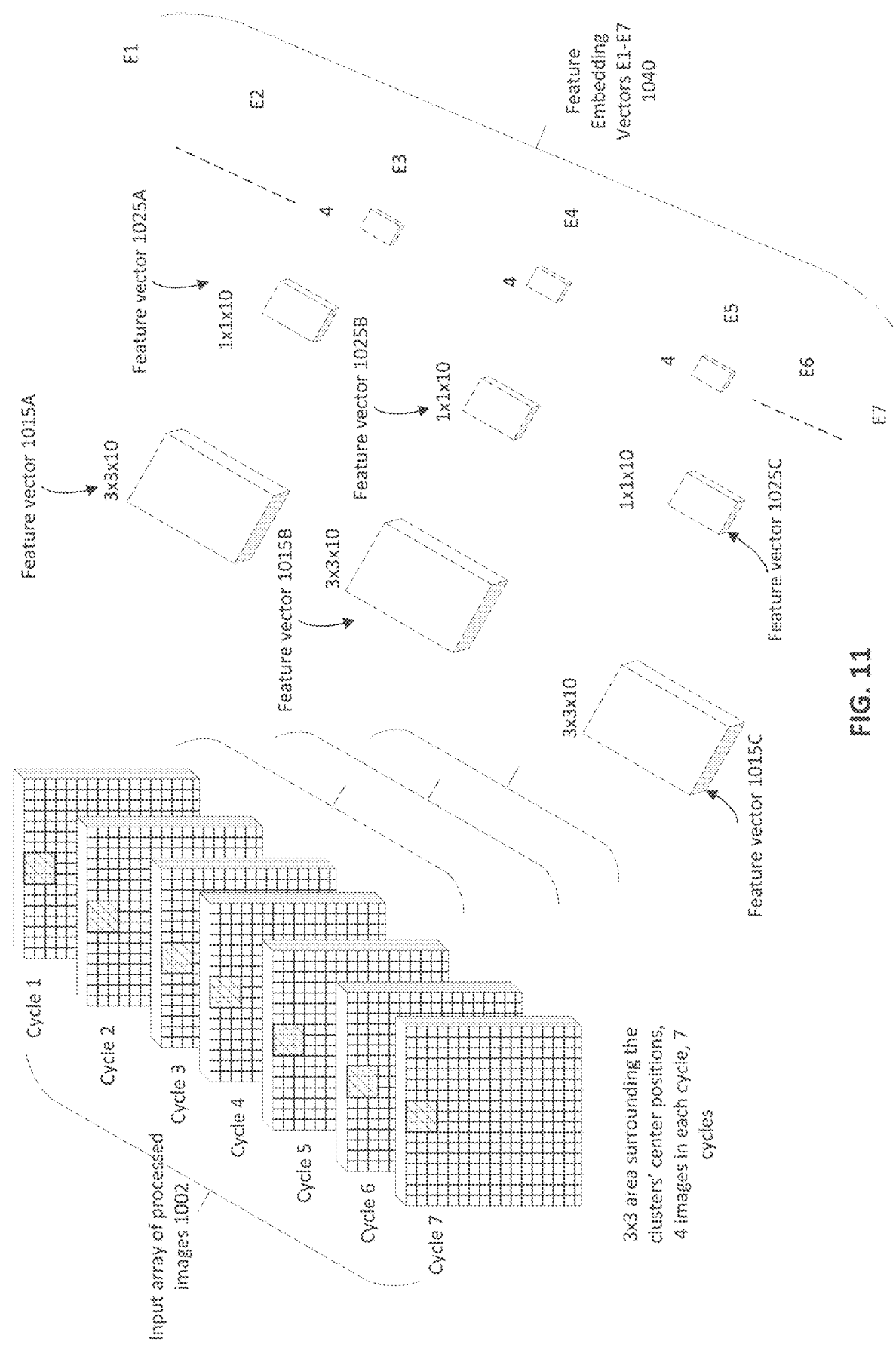
FIG. 11 illustrates a feature extraction pipeline in accordance with one embodiment of the present invention.

Based on the center positions of clusters, another trained convolution neural network extracts features from a window, e.g., 3×3, 5×5, etc., around the cluster center) applied to the selected set of processed images to generate feature embedding vectors. FIG. 10 is a block diagram illustrating an exemplary feature extraction process 1000 using a trained CNN 1008 in accordance with one embodiment of the present invention. FIG. 11 illustrates the input array, intermediate feature vectors, and output embedding vectors in an exemplary feature extraction pipeline. Referencing FIGS. 10 and 11, a set of images that have been processed (e.g., using method 400) is provided to a trained CNN 1008 for feature extraction. A window (e.g., 3×3 or 5×5) is applied to the set of images using the detected cluster center. For example, the window may be applied around the detected cluster center, thereby enhancing the feature extraction process by focusing on the detected clusters. Using the center positions of the clusters, the clusters of fluorescent signals are identified in the set of processed images FIGS. 10 and 11 illustrate one example of the input array 1002 as including a set of twenty-eight processed images corresponding to images captured in seven consecutive synthesis cycles using a four-fluorescence channel configuration.

As shown in FIG. 10, in one embodiment, CNN 1008 includes three convolution layers 1010, 1020, and 1030. To extract features, a window size is selected. The window size can be measured by height and width in pixels, for example, 3×3, 5×5, etc. As shown in FIGS. 10 and 11, using the selected window size, first convolution layer 1010 performs convolution operations on the processed images of input array 1002 using selected set of images of fluorescent signals. In one embodiment, the convolution operations are performed to a subset of processed images corresponding to images obtained in, for example, five out of seven consecutive cycles. For instance, as shown in FIG. 11, convolution operations are performed on the 20 processed images obtained for cycles 1-5 to generate a feature vector 1015A. Similarly, convolution operations are performed on the 20 processed images of cycles 2-6 to generate a feature vector 1015B; and convolution operations are performed on the 20 processed images of cycles 3-7 to generate a feature vector 1015C. Each of feature vectors 1015A-C (collectively as 1015) has reduced dimensions of 3×3×10. The convolution operations are performed similar to that described above (e.g., slide a kernel having the preconfigured window size through the images). It is understood that FIG. 11 only illustrates seven cycles, but other features vectors 1015 can be generated in a similar manner by using one or more other cycles not shown in FIG. 11.

As shown in FIG. 11, feature vectors 1015A-C are used as input vectors to second convolution layer 1020. Convolution operations are performed on feature vectors 1015A-C to generate feature vectors 1025A-C. Each of feature vectors 1025A-C (collectively as 1025) has a further reduced dimension of 1×1×10. It is understood that FIG. 11 only illustrates three feature vectors 1025A-C and other features vectors 1025 can be generated in a similar manner by using one or more other feature vectors 1015 not shown in FIG. 11. The convolution operations are performed similar to that described above (e.g., slide a kernel having the preconfigured window size through the images).

In turn, feature vectors 1025A-C are used as input vectors to third convolution layer 1030. Convolution operations are performed on feature vectors 1025A-C to generate feature embedding vectors 1040 E3, E4, and E5, respectively. Each of feature embedding vectors 1040 E3, E4, and E5 (collectively as embedding vectors 1040) is a one-dimensional vector having a dimension of four (i.e., a vector having four elements), thereby further reducing the dimensions of the feature vectors. It is understood that FIG. 11 only illustrates three feature embedding vectors E3, E4, and E5, and other features vectors (e.g., E1, E2, E6, and E7) can be generated by using one or more other feature vectors 1025 not shown in FIG. 11. Zero padding may be used for generating beginning or ending feature embedding vectors. In some embodiments, CNN 1008 is trained in a similar manner as described above for CNN 900 (e.g., iteratively adjust weights to obtain output vectors as close as predicted or known ones).

Attention-Based Deep Learning Model for Basecalling

Figure 12:
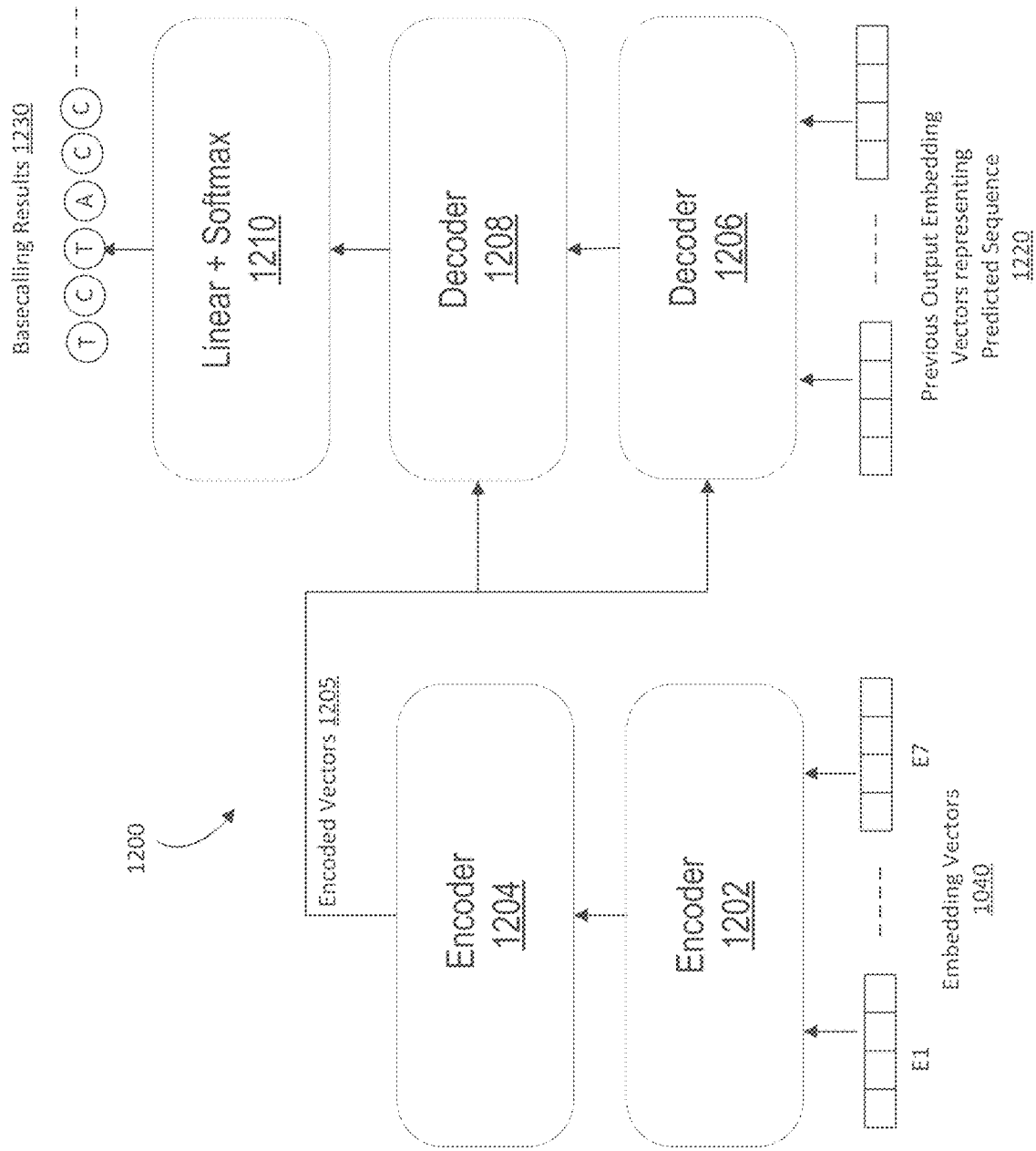
FIG. 12 is a block diagram illustrating an exemplary transformer neural network in accordance with one embodiment of the present invention.

Feature embedding vectors 1040 E1-E7 includes seven 1-dimensional vectors, each having four elements. Therefore, vectors 1040 have a total dimension of 7×4, representing the extracted cluster information of the four images captured in the seven consecutive synthesis cycles. In some embodiments, the feature embedding vectors 1040 are provided to a trained transformer neural network for basecalling. FIG. 12 is a block diagram illustrating a transformer neural network 1200 in accordance with one embodiment of the present invention. In the example shown in FIG. 12, the input to network 1200 includes seven 1-dimensional feature embedding vectors. Each of the feature embedding vectors has four elements. A transformer neural network has an encoder-decoder architecture using one or more attention layers. A transformer neural network can process multiple input sequences or vectors in parallel. Therefore, both the processing efficiency and speed of training of the network are greatly improved. Further, a transformer neural network uses one or more multi-headed attention layers for better interpreting or emphasizing on the important aspects of the input embedding vectors. The vanishing gradient issue is also eliminated or significantly reduced by the transformer neural network.

Figure 13:
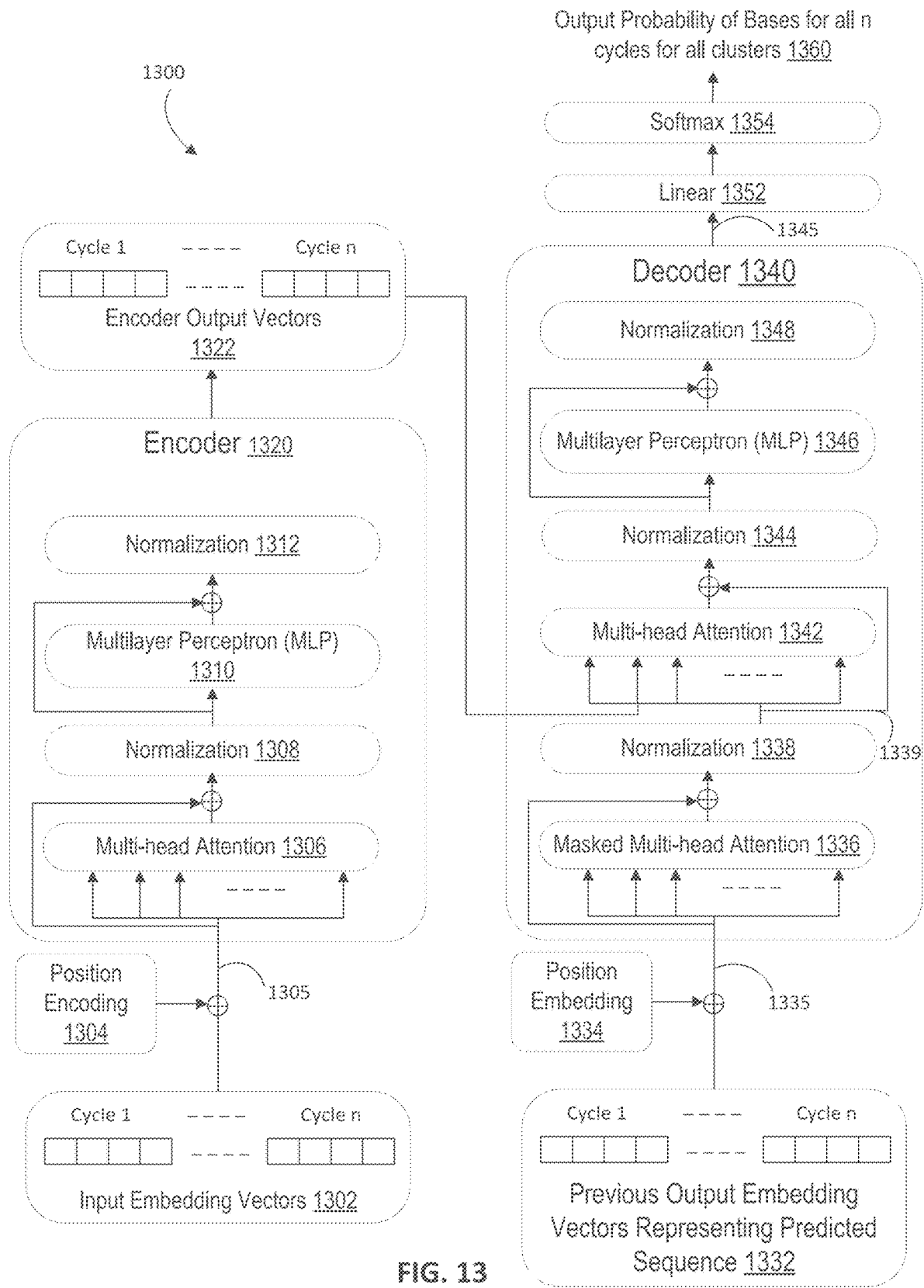
FIG. 13 is a block diagram illustrating a configuration of an exemplary transformer neural network in accordance with one embodiment of the present invention.

Referencing FIG. 12, network 1200 includes two encoders 1202 and 1204, two decoders 1206 and 1208, and a linear and Softmax layer 1210. A trained network 1200 can estimate the probabilities of bases corresponding to the clusters of fluorescent signals in each cycle. FIG. 13 is a block diagram illustrating details of a configuration of an exemplary transformer neural network 1300. A part or entire network 1300 can be used to implement network 1200. Network 1300 uses one encoder 1320 and one decoder 1340 as illustration. It is understood that additional encoder(s) and/or decoder(s) can have similar configurations. For example, both encoders 1202 and 1204 shown in FIG. 12 can have the same or similar configuration as encoder 1320 shown in FIG. 13. Similarly, both decoders 1206 and 1208 shown in FIG. 12 can have the same or similar configuration as decoder 1340 shown in FIG. 13. It is further understood that any number of encoders and decoders may be configured as desired to optimize the performance of a transformer neural network.

Referencing FIG. 13, network 1300 obtains input embedding vectors 1302 as inputs. The input embedding vectors 1302 are vectors generated by the feature extraction process as described above. Thus, the input embedding vectors 1302 are vectors representing features extracted from the images captured in "n" synthesis cycles (e.g., vectors 1040 E1-E7 for 7 cycles as shown in FIG. 11). The elements of these feature embedding vectors correspond to fluorescent signal intensities associated with different nucleotide bases. In the example shown in FIG. 13, each input embedding vector 1302 is a one-dimensional vector having four elements. Multiple embedding vectors can form an embedding space. Within the embedding space, vector elements are assigned with particular values. Vector elements having the same or similar values are grouped close to each other in the embedding space.

Network 1300 includes a position encoding layer 1304. The input embedding vectors 1302 are provided to the position encoding layer 1304 to account for the order of the feature vector elements. The position encoding layer 1304 includes a positional encoder, which is a vector that provides context according to the position of the elements in the vector. The position encoding layer 1304 generates position encoded vectors 1305.

The position encoded vectors 1305 are then provided to encoder 1320, which is a self-attention based encoder. Encoder 1320 includes a multi-head attention layer 1306. The multi-head attention layer 1306 determines multiple attention vectors per element of the position encoded vectors 1305 and takes a weighted average to compute a final attention vector for each element of the position encoded vectors 1305. The final attention vectors capture the contextual relationship between elements of the position encoded vectors 1305.

As shown in FIG. 13, encoder 1320 also includes one or more normalization layers 1308 and 1312. The normalization layers control the gradient scales. In some embodiments, the normalization layer 1308 is positioned after the multi-head attention layer 1306, as illustrated in FIG. 13. In some embodiments, the normalization layer can be positioned before the multi-head attention layer. Similarly, it can be positioned before or after multiplayer perceptron layer 1310 as well. A normalization layer standardizes the inputs to the next layer, which has the effect of stabilizing the network's learning process and reducing the number of training iterations required to train the deep learning network. Normalization layer 1308 and 1312 can perform batch normalization and/or layer normalization.

FIG. 13 also illustrates that encoder 1320 includes a multilayer perceptron (MLP) 1310. MLP 1310 is a type of feedforward neural network. An MLP has layers of nodes including: an input layer, one or more hidden layers, and an output layer. Except for the input nodes, each node in an MLP is a neuron that uses nonlinear activation function. MLP 310 is applied to every normalized attention vector. MLP 1310 can transform the normalized attention vectors to a form that is acceptable by the next encoder or decoder in network 1300. In the example shown in FIG. 13, one encoder is used. Thus, in FIG. 13, the output of MLP 1310, after normalized by normalization layer 1312, is the encoder output vectors 1322. Encoder output vectors 1322 are then provided to the decoder 1340. In the example shown in FIG. 12, a stacked encoder structure having two encoders 1202 and 1204 is used. Thus, the output vectors from encoder 1202 are provided to the next encoder 1204 as input vectors.

Unlike using a typical RNN, all the attention vectors (or those after normalization) are independent from one another. Therefore, they can be provided to the MLP 1310 in parallel. Encoder 1320 can thus generate encoder output vectors 1322 for all the input embedding vectors 1302 in parallel, thereby significantly improving the processing speed.

Continuing with the example shown in FIG. 13, the encoder output vectors 1322 are provided to a decoder 1340. Similar to encoder 1320, decoder 1340 has a multi-head attention layer 1342, a MLP layer 1346, and normalization layers 1344 and 1348. These layers are similar to those of encoder 1320 described above and are thus not repeatedly described. Decoder 1340 further includes a masked multi-head attention layer 1336, which is used in training transformer neural network 1300. In training network 1300, input embedding vectors 1302 (after position encoding) are provided to the encoder 1320 and previous output embedding vectors 1332 (after position encoding) are provided to the decoder 1340. Input embedding vectors 1302 represent unknown nucleic acid sequences and previous output embedding vectors 1332 represent known or previously-predicted nucleic acid sequences. Position encoding of previous output embedding vectors 1332 is performed to generate position encoded vectors 1335, in a similar manner as generating the position encoded vectors 1305 for encoder 1302. The position encoded vectors 1335 are provided to masked multi-head attention layer 1336, which generates attention vectors to represent how much each element in a position encoded vector 1335 is related to other elements in the same vector.

In the training process, an element in an input embedding vector 1302 is transformed to an element in the encoder output vector 1322 using encoder 1320. The element in the encoder output vector 1322 is compared with a corresponding element in a previous output embedding vector 1332, which represents a known or previously predicted nucleic acid sequence. After the comparison, the network 1300 updates its matrix of weight values. This process is performed in iterations so that the corresponding elements in encoder output vector 1322 and previous output embedding vector 1332 are matched as close as possible. In the training process, however, all elements in an input embedding vector 1302 can be considered for predicting a next element in a decoder output vector 1345. But for a previous output embedding vector 1332, only previously-considered elements in the vector 1332 can be used. This is because network 1300 is trying to predict the next element and decoder 1340 cannot be given the actual known or predicted next element from the previous output embedding vector 1332. As such, masked multi-head attention layer 1336 masks or hides those elements that are considered later in the training process by transforming them into 0's to that the multi-head attention layer 1342 does not use them. After training, when the network 1300 operates to generate decoder output vectors 1345 for given input embedding vectors 1302, only output embedding vectors generated in the previous iterations are available to network 1300. Thus, masked multi-head attention layer 1336 can function as a normal multi-head attention layer without having to mask or hide any elements.

Masked multi-head attention 1336 generates attention vectors, which are passed to normalization layer 1338. After that, normalized attention vectors 1339 are provided to multi-head attention layer 1342. As described above, the encoder output vectors 1322 are also provided to multi-head attention layer 1342. Multi-head attention layer 1342 then compares an encoder output vector 1322 and a corresponding normalized attention vector 1339 by mapping the corresponding elements in both vectors and determining the relation between them. The output of multi-head attention layer 1342 is attention vectors for every element in both input vectors 1322 and 1339 (representing an unknown sequence and a known sequence), with each such attention vector representing the relationship with other elements in both vectors 1322 and 1339.

Next, attention vectors generated by multi-head attention layer 1342 (after normalization by normalization layer 1344) are provided to MLP layer 1346, which transform the attention vectors to a form that is acceptable by the next layer in network 1300. The output of the MLP layer 1346 is normalized by normalization layer 1348 and then passed to linear layer 1352. A linear layer is another type of feed-forward layer capable of learning an offset and a rate of correlation between the input and output of the linear layer. The linear layer can learn scaling automatically such that it can reduce or expand dimensions of the input vectors.

Finally, the output from linear layer 1352 is passed to a Softmax layer 1354, which transforms its input to probability distributions representing probabilities of bases. And a particular base is predicted using the highest probability for that base. The process is repeated many times to produce basecalling results (e.g., results 1230 shown in in FIG. 12), which include sequences of DNA fragments. Similar to those described for encoder 1320, decoder 1340 can also process attention vectors in parallel. Therefore. probabilities of bases for all clusters of fluorescent signals captured in the images in "n" cycles can be predicted in parallel. This greatly reduces the processing time for basecalling.

As described above, a trained transformer neural network 1300 starts by generating input embedding vectors 1302 representing features of clusters of fluorescent signals of all images captured in "n" synthesis cycles. Using self-attention mechanism implemented by multi-head attention 1306, network 1300 aggregates information from all of the features represented by input embedding vectors 1302 to generate encoder output vectors 1322. Each encoder output vector 1332 is thus informed by the entire context. The generation of the multiple encoder output vectors 1322 are performed in parallel for all features represented by input embedding vectors 1302. Decoder 1340 attends not only to the encoder output vectors 1322 but also other previously generated embedding vectors 1332. Network 1300 can be trained with sufficient data to provide a high accuracy. The training of network 1300 can also be repeated or updated over time to maintain or provide even higher accuracy.

Figure 14:
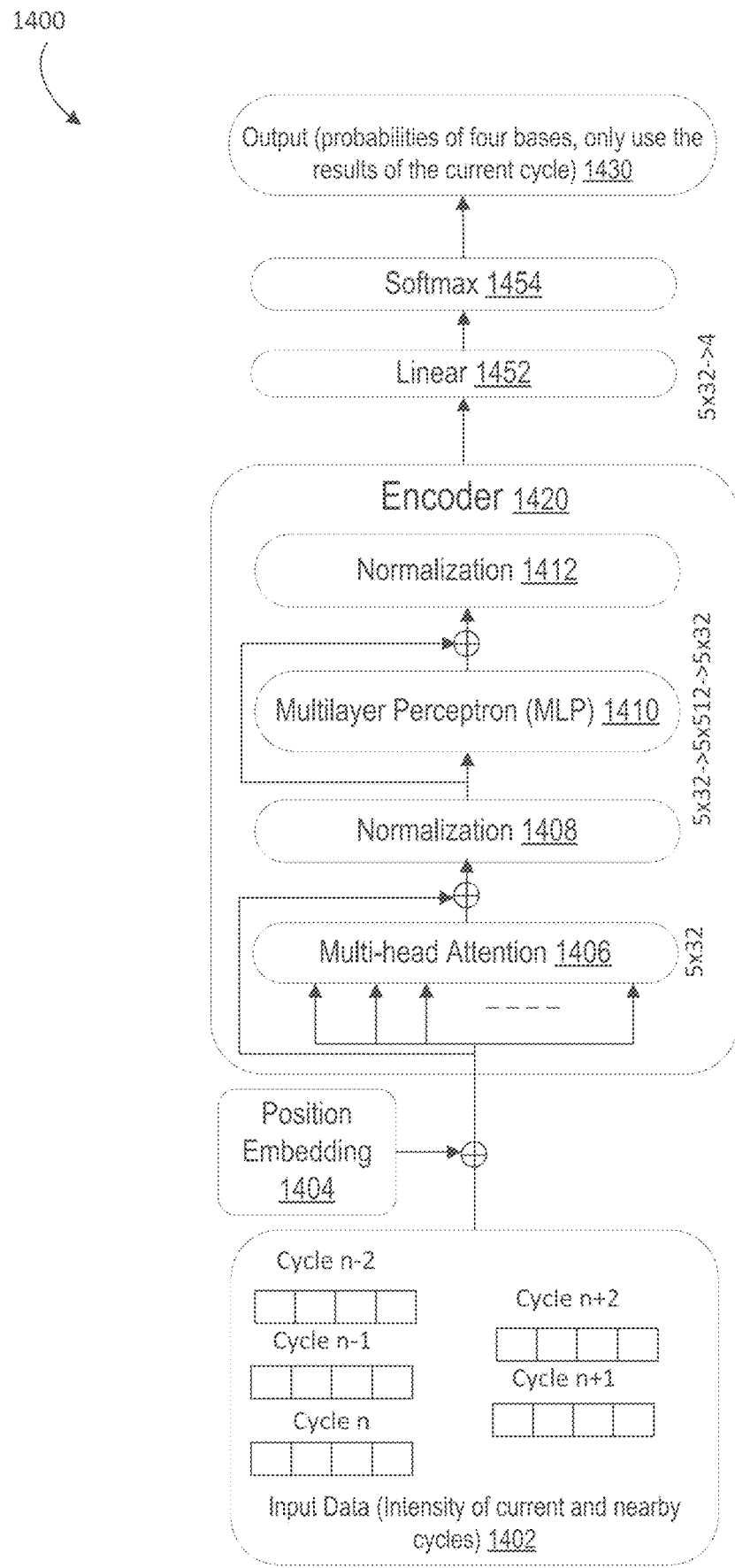
FIG. 14 is a block diagram illustrating a configuration of an exemplary attention-based neural network in accordance with one embodiment of the present invention.

FIG. 14 is a block diagram illustrating a configuration of another exemplary attention-based neural network 1400 in accordance with one embodiment of the present invention. Network 1400 is provided with input data 1402. Input data 1402 include input vectors that represent clusters of fluorescent signals from the current synthesis cycle "n" and its nearby cycles (e.g., the "n–2", "n–1", "n+1", and "n+2" cycles). It is understood that any number of nearby cycles can be used (e.g., 2, 4, 6, etc.). Compared to network 1300, the input vectors for network 1400 may use the cluster detection results directly without having to extracting features. Thus, the feature extraction process 1000 shown in FIG. 10 can be skipped. Detected clusters (and their center positions) can be directly represented by vectors and used as input to network 1400.

In some embodiment, input data 1402 also include weight matrices (e.g., 3) that are dotted to produce three matrices of queries, keys, and values, represented by K, Q, and V respectively. The input vectors are position encoded using position embedding layer 1404 similar to those described above. Multi-head attention layer 1406 computes attention vectors by the following formula (eq. 1).

$$\text{Attention}(Q, K, V) = \text{softmax}\left(\frac{QK^T}{\sqrt{d_k}}\right)V \qquad [\text{eq. 1}]$$

In equation 1, $d_k$ denotes the dimension of queries and keys, and T denotes matrix transformation. Equation 1 can also be used for computing attention vectors for any of the other self-attention based network such as network 1300. In one example, if $d_k$ is configured to be 32, then the dimensions of the output of multi-head attention layer 1406 are 5×32.

In one embodiment, MLP layer 1410 in encoder 1420 has two layers (e.g., the hidden layer and the output layer). MLP layer 1410 can process each attention vector independently. In one example, a hidden layer in MLP layer 1410 has a dimension of 512. The output layer in MLP layer 1410 may have a dimension that is the same as the input to MLP layer 1410. In other words, the dimensional change from the input of MLP layer 1410 to the hidden layer output is from 5×32 to 5×512; and the dimensional change from the hidden layer output to the output of the MLP layer 1410 is from 5×512 to 5×32. The output of the MLP layer 1410, after normalization by normalization layer 1412, is provided to linear layer 1452 and then to Softmax layer 1454. These layers are similar to linear layer 1352 and Softmax layer 1354, respectively, and are thus not repeated described here. The final output includes probabilities of the four bases of a particular cluster for the current cycle "n" (corresponding to the four images captured in a four-channel configuration).

Comparing to network 1300, network 1400 has only one or more encoders but no decoder. While FIG. 14 only illustrates one encoder 1420, one or more additional encoders can be used in a stacked manner. Network 1400 can further improve the basecalling speed and efficiency than network 1300. As described above, network 1400 does not need to perform feature extraction and also does not include a decoder. Therefore, the basecalling process can be performed faster by using network 1400 than by using network 1300. In some circumstances, the basecalling process using network 1400 may be slightly less accurate than using network 1300. However, such slight decreasing in accuracy (measured by error rate) may be acceptable in some nucleic acid sequencing applications (e.g., if the accuracy is nonetheless sufficient to identify a person-of-interest in a forensic analysis).

One-Dimensional Convolution Based Deep Learning Model for Basecalling

Figure 15:
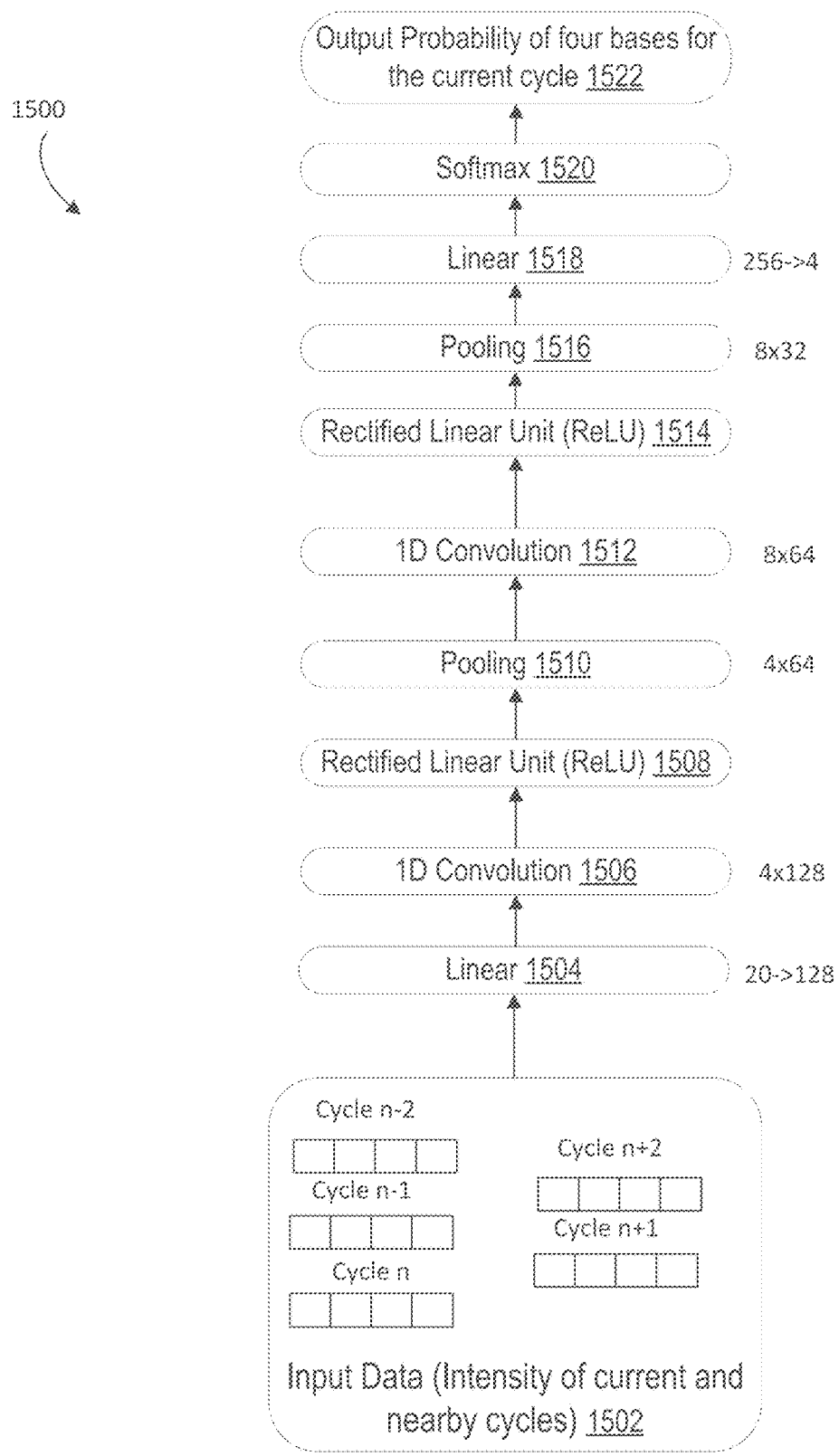
FIG. 15 is a block diagram illustrating a configuration of an exemplary 1-dimensional convolution based neural network in accordance with one embodiment of the present invention.

FIG. 15 is a block diagram illustrating a configuration of an exemplary 1-dimensional convolutional neural network 1500 in accordance with one embodiment of the present invention. Network 1500 is provided with input data 1502. Input data 1502 include input vectors that represent clusters of fluorescent signals from the current synthesis cycle "n" and its nearby cycles (e.g., the "n−2", "n−1", "n+1", and "n+2" cycles). It is understood that any number of nearby cycles can be used (e.g., 2, 4, 6, etc.). Compared to network 1300, the input vectors for network 1500 may use the cluster detection results directly without having to extracting features. Thus, the feature extraction process 1000 shown in FIG. 10 can be skipped. Detected clusters (and their center positions) can be directly represented by vectors and used as input to network 1500.

Compared to network 1400, network 1500 may not have an attention layer. In the example shown in FIG. 15, network 1500 includes one or more linear layer (e.g., layers 1504 and 1518), one or more 1-dimensional convolution layers (e.g., layers 1506 and 1512), one or more rectified linear unit (ReLU) layers (e.g., layers 1508 and 1514), one or more pooling layers (e.g., 1510 and 1516), and a Softmax layer 1520. The linear layer(s), pooling layers, and the Softmax layer are the same or similar to those described above and are not repeatedly described. A Rectified Linear Unit (ReLU) layer implements an ReLU function, which is a type of activation function for introducing non-linearity into the output of a neuron. A 1-dimensional convolution layer performs convolution operations in one direction, rather than two directions in a 2-dimensional convolution layer. For example, the input to 1-dimensional convolution layers 1506 and 1512 are both 1-dimensional vectors (e.g., 1D feature vector representing signals at the cluster center).

In some embodiments, each of the 1-dimensional convolution layers 1506 and 1512 has a kernel for performing convolution operation. The kernel may have, for example, a size of 4 and a stride of 1. The stride is the number of pixels shifts over the input matrix. Therefore, if the stride is 1, the kernel (or filter) is moved 1 pixel at a time. In some embodiments, to keep the size of features constant, the padding may be configured to be 3, one at the head and two at the tail. A padding refers to the number of pixels added to an image when it is being processed by the kernel of the 1-dimensional convolution layer.

FIG. 15 also illustrates exemplary dimensions associated with each layer in network 1500. For example, the input vector may have 20 elements corresponding to five consecutive cycles and four elements for each cycle. The linear layer 1504 generates an output having a dimension of 128. The 1D convolution layer 1506 generates an output having a dimension of 4×128. The pooling layer 1510 reduces the dimension to 4×64 (the pooling may use average pooling or max pooling). The 1D convolution layer 1512 generates an output having a dimension of 8×64. The pooling layer 1510 reduces the dimension to 8×32. The linear layer 1518 takes the input of 8×32 (i.e., 256) and reduces it to a dimension of 4. The Softmax layer 1520 generates the probabilities of the four bases of a particular cluster for the current cycle "n" (corresponding to the four images captured in a four-channel configuration). The process can be repeated many times in parallel to generate probabilities of the bases of multiple clusters.

Comparing to network 1300, network 1500 does not require using an attention mechanism. Network 1500 also does not need feature extraction to be performed and can use the cluster detection results for generating the input vectors to network 1500. Network 1500 can thus further improve the basecalling speed and efficiency than network 1300. Therefore, the basecalling process can be performed faster by using network 1500 than by using network 1300. In some circumstances, the basecalling process using network 1500 may be slightly less accurate than using network 1300. However, such slight decreasing in accuracy (measured by error rate) may be acceptable in some nucleic acid sequencing applications (e.g., if the accuracy is nonetheless sufficient to identify a person-of-interest in a forensic analysis).

Automated Data Labelling for Training Deep Learning Models for Basecalling

Figure 16:
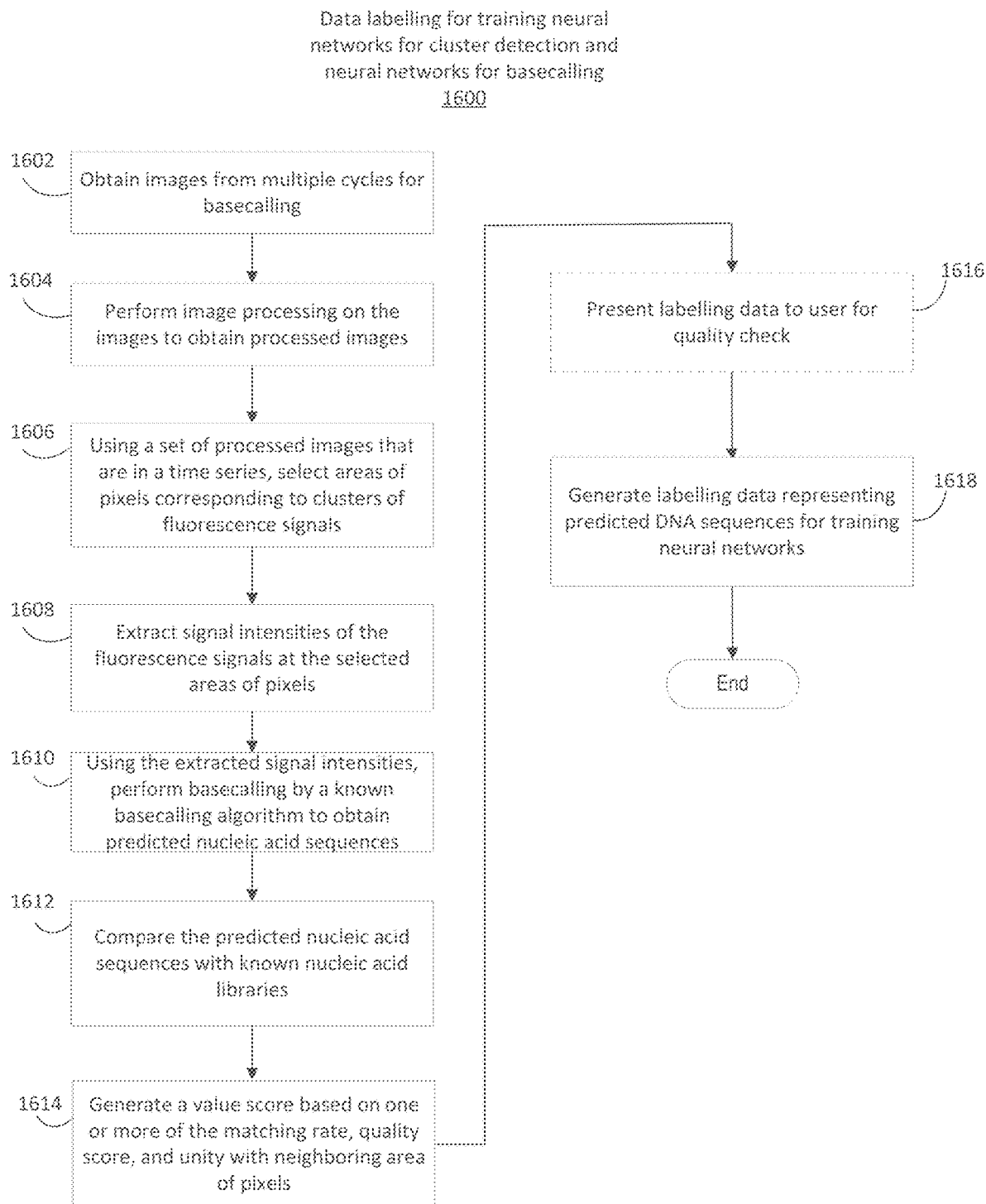
FIG. 16 is a flowchart illustrating a method of data labelling for training neural networks for cluster detection and neural networks for basecalling in accordance with an embodiment of the present invention.

As described above, the cluster detection neural networks (e.g., network 1000) and basecalling neural networks (e.g., networks 1300, 1400, and 1500) require training before they can be used for cluster detection or basecalling. For training the various neural networks, for example, known or previously-predicted basecalling results are needed for generating the previous output embedding vectors 1332. Traditionally, the known or previously-predicted basecalling results are generated by a manual data labelling process. This manual data labelling process is rather slow, inefficient, and sometimes impractical if there is a large quantity of sequences. Therefore, a better and more efficient datal labelling process is needed. FIG. 16 is a flowchart illustrating such an exemplary data labelling method 1600 for training neural networks.

Referencing FIG. 16, step 1602 of method 1600 obtains images from multiple synthesis cycles for basecalling. Step 1604 performs image processing on the obtained images and generates processed images. Steps 1602 and 1604 are the same or substantially similar to steps 302 and 304, respectively, of method 300 as described above and are thus not repeatedly described. Step 1606 of method 1600 selects areas of pixels corresponding to clusters of fluorescent signals using a set of processed images. As one example, all pixels that are located in a cluster area may be selected from a processed image. And this process can be repeated to select pixels for all clusters in all processed images. The selection of areas of pixels can be performing using, for example, previously-obtained data or experimental data. For example, if previously-obtained or experimental data indicate that certain pixel areas mostly do not have detectable fluorescent signals, these pixels may not be selected. As another example, selecting of the pixels may also use a predetermined signal intensity threshold. If a measured signal intensity of a pixel is above the threshold, the pixel is selected. In some embodiments, all pixels may be selected. The selection process can also be performed in other manners using other known cluster identification methods.

Method 1600 further includes step 1608 for extracting signal intensities of the fluorescent signals at the selected areas of pixels. Step 1608 can be performed by, for example, integrating the signals in a pixel area and repeating for all selected pixels. Extracting signal intensities can also be performed in any other manner using known signal intensity extraction methods (e.g., summing, taking the maximum signal value, taking an average, normalization, etc.).

Using the extracted signal intensities, step 1610 performs basecalling by using a known basecalling algorithm to obtain predicted nucleic acid sequences. Such known basecalling algorithms may be, for example, the AYB (All Your Base) basecalling algorithm, which uses an explicit statistical model of how errors occur during sequencing to produce more accurate reads from the raw intensity data. Such known basecalling algorithms may also include, for example, algorithms based on a combination of CNN and RNN networks, a combination of CNN and LSTM networks, a combination of CNN, RNN/LSTM and CTC networks, etc.

Next, step 1612 of method 1600 compares the predicted nucleic acid sequences with known nucleic acid libraries to compute one or more of a matching rate, a quality score, and a unity with neighboring area of pixels. The known nucleic acid libraries may be generated by analyzing the same or similar samples using, for example, a Sanger sequencing algorithm or any other sequencing algorithms. A matching rate indicates how well the predicted sequence matches with the sequence in the known nucleic acid libraries. Mismatch between bases in a sequence reduces the matching rate. A quality score is another indication of the basecalling accuracy. For example, a Phred quality score (Q score), which indicates the probability that a given base is called incorrectly by the sequencer, can be used to assess the overall accuracy of a sequencing platform. The predicted nucleic acid sequences corresponding to pixels belonging to an independent cluster area should have a good matching rate and a high quality score. Moreover, the sequences of adjacent pixels should be the same or substantially similar. In contrast, the matching rate of a predicted sequence corresponding to pixels belonging to a blank area or a cluster overlapping area should be low. In step 1614, one or more of the matching rate, the quality score, and the unity with neighboring area of pixels can be used to generate a value score, which is an overall indication of the result of comparison between the predicted nucleic acid sequences and known nucleic acid libraries.

The predicted nucleic acid (e.g., DNA) sequences may be used as labelling data if they have a sufficiently high matching rate, quality score, unity with neighboring area of pixels, and/or a value score. In some embodiments, an option step 1616 provides the labelling data to a user for a manual quality check. If there are any corrections of bases or sequences need to be made, step 1616 further provides a user interface to receive inputs from the user for making the corrections. Method 1600 then proceeds to step 1618 to generate labelling data (with or without user corrections) representing predicted nucleic acid sequences for training the neural networks (e.g., the neural networks for cluster detection and the neural networks for basecalling described above). Based on the comparison results as indicated by the matching rate, quality score, unity with neighboring area of pixels, and/or the overall value score, the pixels can be classified to generate labels for the predicted bases and sequences. As shown in FIG. 16, in some embodiments, step 1620 determines if more images are used for data labelling. If so, the process repeats from step 1602. If there are no more images, the process ends. After the user is satisfied with the labelling data, these data can be used for training transformer-based neural network 1300. It is understood that while data labelling method 1600 is described with respect to training transformer-based neural network 1300, it can also be used to generate labeling data for other neural networks such as networks 1400 and 1500.

Additional embodiments are described below. In some embodiments of the invention, a computer-implemented method for determining a plurality of sequences of nucleic acid (e.g., DNA) molecules in a sequencing-by-synthesis process is provided. The method comprises obtaining images of fluorescent signals obtained in a plurality of synthesis cycles. The images of fluorescent signals are associated with a plurality of different fluorescence channels. The method further comprises preprocessing the images of fluorescent signals to obtain processed images. Based on a set of the processed images, the method further comprises detecting center positions of clusters of the fluorescent signals using a trained convolutional neural network (CNN) and extracting, based on the center positions of the clusters of fluorescent signals, features from the set of the processed images to generate feature embedding vectors. The method further comprises determining, in parallel, the plurality of sequences of DNA molecules using the extracted features based on a trained attention-based neural network.

In some embodiments, preprocessing the images of fluorescent signals to obtain processed images comprises performing light correction of one or more of the images. Performing the light correction of one or more of the images comprises one or both of performing a Gamma correction and a homomorphic filtering.

In some embodiments, preprocessing the images of fluorescent signals to obtain processed images comprises performing image registration of images obtained for different synthesis cycles of the plurality of synthesis cycles. Performing the image registration of images obtained for different synthesis cycles of the plurality of synthesis cycles comprises selecting a reference synthesis cycle from the plurality of consecutive synthesis cycles; aligning images obtained for other synthesis cycles of the plurality of synthesis cycles to respective images obtained for the reference synthesis cycle by registering at a pixel level; and adjusting alignments of the images by applying offsets caused by at least one of system variations and environmental variations.

In some embodiments, preprocessing the images of fluorescent signals to obtain processed images comprises performing image registration of images obtained using different fluorescence channels. In some embodiments, preprocessing the images of fluorescent signals to obtain processed images comprises performing image enhancement of the images. Performing image enhancement of the images comprises one or more of performing a smoothing operation, an edge detection operation, and a Laplace of Gaussian operation.

In some embodiments, based on the set of the processed images, detecting center positions of the clusters of the fluorescent signals using the trained convolutional neural network (CNN) comprises selecting the set of processed images from the processed images. The set of processed images includes processed images obtained corresponding to at least some of the plurality of synthesis cycles. Detecting center positions of the clusters of the fluorescent signals further comprises using the trained CNN, generating a feature map based on the set of the processed images, the feature map representing clusters of fluorescent signals represented in the set of processed images; and detecting the center positions of the clusters of the fluorescent signals by performing local maxima operations of the feature map.

In some embodiments, the trained CNN for cluster detection comprises one or more convolution and activation layers, one or more down sampling layers, one or more up sampling layers, and one or more skip connections. In some embodiments, the trained CNN is a first trained CNN. Extracting features from the set of the processed images based on the center positions of the clusters of fluorescent signals comprises selecting a window size for extracting the features; and generating feature embedding vectors by applying the selected window size to the set of processed images using a second trained CNN. The set of processed images includes images obtained in at least some of the plurality of synthesis cycles.

In some embodiments, determining, in parallel, the plurality of sequences of nucleic acid molecules using the extracted features based on the trained attention-based neural network comprises providing the feature embedding vectors to the trained attention-based neural network; estimating, by the trained attention-based neural network using the feature embedding vectors, probabilities of bases corresponding to the clusters of fluorescent signals; and determining the plurality of sequences based on the probabilities of bases corresponding to the clusters of fluorescent signals.

In some embodiments, the trained attention-based neural network comprises one or more self-attention based encoders and one or more self-attention based decoders. A self-attention based encoder of the one or more self-attention based encoders comprises a multi-head attention layer, a multilayer perceptron layer, and one or more normalization layers.

In some embodiments, the trained attention-based neural network comprises one or more self-attention based encoders without a decoder. Determining, in parallel, the plurality of sequences of nucleic acid molecules using the extracted features based on a trained attention-based neural network comprises providing the feature embedding vectors to the trained attention-based neural network. The feature embedding vectors represent signal intensities of a current synthesis cycle and a plurality of neighboring synthesis cycles. Determining the plurality of sequences of nucleic acid molecules further comprises estimating, by the trained attention-based neural network using the feature embedding vectors, probabilities of bases corresponding to the clusters of fluorescent signals of the current synthesis cycle; and determining the plurality of sequences of nucleic acid molecules based on the probabilities of bases corresponding to the clusters of fluorescent signals.

In some embodiments of the invention, a computer-implemented method for determining a plurality of sequences of nucleic acid (e.g., DNA) molecules in a sequencing-by-synthesis process is provided. The method comprises obtaining images of fluorescent signals obtained in a plurality of synthesis cycles. The images of fluorescent signals are associated with a plurality of different fluorescence channels. The method further comprises preprocessing the images of fluorescent signals to obtain processed images. The method further comprises based on a set of the processed images, detecting center positions of clusters of the fluorescent signals using a trained convolutional neural network (CNN). The method further comprises extracting, based on the center positions of the clusters of fluorescent signals, features from the set of the processed images to generate feature embedding vectors. The method further comprises determining, in parallel, the plurality of sequences of nucleic acid molecules using the extracted features based on a trained 1-dimensional convolution-based neural network.

In some embodiments, the trained 1-dimensional convolution based neural network comprises one or more 1-dimensional convolutional layers and one or more rectified linear unit (ReLU) layers. In some embodiments, determining, in parallel, the plurality of sequences of nucleic acid molecules based on a trained 1-dimensional convolution-based neural network comprises providing the feature embedding vectors to the trained 1-dimensional convolution-based neural network. The feature embedding vectors represent signal intensities of a current synthesis cycle and a plurality of neighboring synthesis cycles. Determining the plurality of sequences of nucleic acid molecules further comprises estimating, by the trained 1-dimensional convolution-based neural network using the feature embedding vectors, probabilities of bases corresponding to the clusters of fluorescent signals of the current synthesis cycle; and determining the plurality of sequences of the nucleic acid molecules based on the probabilities of bases corresponding to the clusters of fluorescent signals.

In some embodiments of the invention, a computer-implemented method for training one or more neural networks used in a process of determining a plurality of sequences of nucleic acid (e.g., DNA) molecules in a sequencing-by-synthesis process is provided. The method comprises obtaining images of fluorescent signals obtained in a plurality of synthesis cycles. The images of fluorescent signals are associated with a plurality of different fluorescence channels. The method further comprises preprocessing the images of fluorescent signals to obtain processed images. The method further comprises extracting signal intensities of the fluorescent signals at selected areas of the processed images. Based on the extracted signal intensities, the method further comprises performing basecalling by using a known basecalling algorithm to obtain predicted nucleic acid sequences. The method further comprises training the one or more neural networks using the predicted nucleic acid sequences.

In some embodiments, the method further comprises prior to extracting the signal intensities of the fluorescent signals, selecting areas of the pixels corresponding to clusters of fluorescent signals to obtain the selected areas.

In some embodiments, training the one or more neural networks based on the predicted nucleic acid sequences comprises comparing the predicted nucleic acid sequences with known nucleic acid libraries to compute one or more of a matching rate, a quality score, and a unity with neighboring area of pixels. The training of the one or more neural networks further comprises generating a value score based on one or more of the matching rate, the quality score, and the unity with neighboring area of pixels; generating labelling data representing the predicted nucleic acid sequences; and training the one or more neural networks using the labelling data.

Exemplary Computing Device Embodiment

Figure 17:
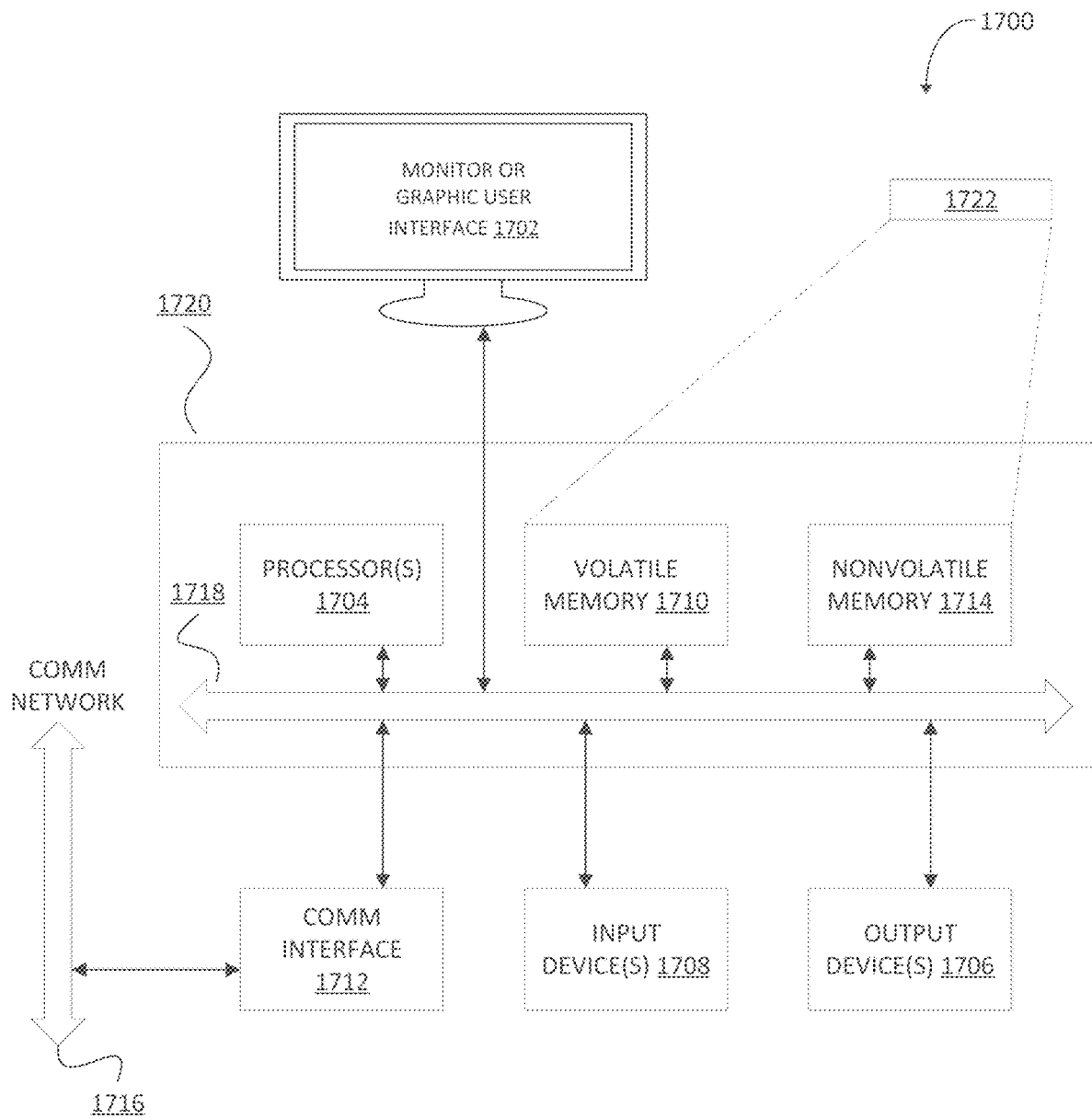
FIG. 17 illustrates a block diagram of an exemplary computing device that may incorporate embodiments of the present invention.

FIG. 17 is an example block diagram of a computing device 1700 that may incorporate embodiments of the present invention. FIG. 17 is merely illustrative of a machine system to carry out aspects of the technical processes described herein, and does not limit the scope of the claims. One of ordinary skill in the art would recognize other variations, modifications, and alternatives. In one embodiment, the computing device 1700 typically includes a monitor or graphical user interface 1702, a data processing system 1720, a communication network interface 1712, input device(s) 1708, output device(s) 1706, and the like.

As depicted in FIG. 17, the data processing system 1720 may include one or more processor(s) 1704 that communicate with a number of peripheral devices via a bus subsystem 1718. These peripheral devices may include input device(s) 1708, output device(s) 1706, communication network interface 1712, and a storage subsystem, such as a volatile memory 1710 and a nonvolatile memory 1717. The volatile memory 1710 and/or the nonvolatile memory 1717 may store computer-executable instructions and thus forming logic 1722 that when applied to and executed by the processor(s) 1704 implement embodiments of the processes disclosed herein.

The input device(s) 1708 include devices and mechanisms for inputting information to the data processing system 1720. These may include a keyboard, a keypad, a touch screen incorporated into the monitor or graphical user interface 1702, audio input devices such as voice recognition systems, microphones, and other types of input devices. In various embodiments, the input device(s) 1708 may be embodied as a computer mouse, a trackball, a track pad, a joystick, wireless remote, drawing tablet, voice command system, eye tracking system, and the like. The input device(s) 1708 typically allow a user to select objects, icons, control areas, text and the like that appear on the monitor or graphical user interface 1702 via a command such as a click of a button or the like. Graphical user interface 1702 can be used in step 1618 of method 1600 to receive user inputs for making the corrections of bases or sequences in a data labelling process.

The output device(s) 1706 include devices and mechanisms for outputting information from the data processing system 1720. These may include the monitor or graphical user interface 1702, speakers, printers, infrared LEDs, and so on as well understood in the art.

The communication network interface 1712 provides an interface to communication networks (e.g., communication network 1716) and devices external to the data processing system 1720. The communication network interface 1712 may serve as an interface for receiving data from and transmitting data to other systems. Embodiments of the communication network interface 1712 may include an Ethernet interface, a modem (telephone, satellite, cable, ISDN), (asynchronous) digital subscriber line (DSL), FireWire, USB, a wireless communication interface such as Bluetooth or WiFi, a near field communication wireless interface, a cellular interface, and the like. The communication network interface 1712 may be coupled to the communication network 1716 via an antenna, a cable, or the like. In some embodiments, the communication network interface 1712 may be physically integrated on a circuit board of the data processing system 1720, or in some cases may be implemented in software or firmware, such as "soft modems", or the like. The computing device 1700 may include logic that enables communications over a network using protocols such as HTTP, TCP/IP, RTP/RTSP, IPX, UDP and the like.

The volatile memory 1710 and the nonvolatile memory 1714 are examples of tangible media configured to store computer readable data and instructions forming logic to implement aspects of the processes described herein. Other types of tangible media include removable memory (e.g., pluggable USB memory devices, mobile device SIM cards), optical storage media such as CD-ROMS, DVDs, semiconductor memories such as flash memories, non-transitory read-only-memories (ROMS), battery-backed volatile memories, networked storage devices, and the like. The volatile memory 1710 and the nonvolatile memory 1714 may be configured to store the basic programming and data constructs that provide the functionality of the disclosed processes and other embodiments thereof that fall within the scope of the present invention. Logic 1722 that implements embodiments of the present invention may be formed by the volatile memory 1710 and/or the nonvolatile memory 1714 storing computer readable instructions. Said instructions may be read from the volatile memory 1710 and/or nonvolatile memory 1714 and executed by the processor(s) 1704. The volatile memory 1710 and the nonvolatile memory 1714 may also provide a repository for storing data used by the logic 1722. The volatile memory 1710 and the nonvolatile memory 1714 may include a number of memories including a main random access memory (RAM) for storage of instructions and data during program execution and a read only memory (ROM) in which read-only non-transitory instructions are stored. The volatile memory 1710 and the nonvolatile memory 1714 may include a file storage subsystem providing persistent (non-volatile) storage for program and data files. The volatile memory 1710 and the nonvolatile memory 1714 may include removable storage systems, such as removable flash memory.

The bus subsystem 1718 provides a mechanism for enabling the various components and subsystems of data processing system 1720 communicate with each other as intended. Although the communication network interface 1712 is depicted schematically as a single bus, some embodiments of the bus subsystem 1718 may utilize multiple distinct busses.

It will be readily apparent to one of ordinary skill in the art that the computing device 1700 may be a device such as a smartphone, a desktop computer, a laptop computer, a rack-mounted computer system, a computer server, or a tablet computer device. As commonly known in the art, the computing device 1700 may be implemented as a collection of multiple networked computing devices. Further, the computing device 1700 will typically include operating system logic (not illustrated) the types and nature of which are well known in the art.

One embodiment of the present invention includes systems, methods, and a non-transitory computer readable storage medium or media tangibly storing computer program logic capable of being executed by a computer processor. The computer program logic can be used to implement embodiments of processes and methods described herein, including method 300 for basecalling, method 400 for image preprocessing, method 800 for cluster detection, method 1000 for feature extraction, and various deep learning algorithms and processes.

Those skilled in the art will appreciate that computer system 1700 illustrates just one example of a system in which a computer program product in accordance with an embodiment of the present invention may be implemented. To cite but one example of an alternative embodiment, execution of instructions contained in a computer program product in accordance with an embodiment of the present invention may be distributed over multiple computers, such as, for example, over the computers of a distributed computing network.

While the present invention has been particularly described with respect to the illustrated embodiments, it will be appreciated that various alterations, modifications and adaptations may be made based on the present disclosure and are intended to be within the scope of the present invention. While the invention has been described in connection with what are presently considered to be the most practical and preferred embodiments, it is to be understood that the present invention is not limited to the disclosed embodiments but, on the contrary, is intended to cover various modifications and equivalent arrangements included within the scope of the underlying principles of the invention as described by the various embodiments referenced above and below.

What is claimed is:

1. A computer-implemented method for determining a plurality of sequences of nucleic acid molecules in a sequencing-by-synthesis process, the method comprising:
   obtaining images of fluorescent signals obtained in a plurality of synthesis cycles, the images of fluorescent signals being associated with a plurality of different fluorescence channels;
   preprocessing the images of fluorescent signals to obtain processed images by performing one or more of:
   light correction of one or more of the images based on one or both of a Gamma correction and a homomorphic filtering,
   image registration of images obtained for different synthesis cycles of the plurality of synthesis cycles,
   image registration of images obtained using different fluorescence channels, and
   image enhancement of the images;
   based on a set of the processed images, detecting center positions of clusters of the fluorescent signals using a trained convolutional neural network (CNN);
   extracting, based on the center positions of the clusters of fluorescent signals, features from the set of the processed images to generate feature embedding vectors; and
   determining, in parallel, the plurality of sequences of nucleic acid molecules using the extracted features based on a trained attention-based neural network.

2. The method of claim 1, wherein performing the image registration of images obtained for different synthesis cycles of the plurality of synthesis cycles comprises:
   selecting a reference synthesis cycle from the plurality of consecutive synthesis cycles;
   aligning images obtained for other synthesis cycles of the plurality of synthesis cycles to respective images obtained for the reference synthesis cycle by registering at a pixel level; and
   adjusting alignments of the images by applying offsets caused by at least one of system variations and environmental variations.

3. The method of claim 1, wherein performing image enhancement of the images comprises one or more of performing a smoothing operation, an edge detection operation, and a Laplace of Gaussian operation.

4. The method of claim 1, wherein based on the set of the processed images, detecting the center positions of the clusters of the fluorescent signals using the trained convolutional neural network (CNN) comprises:
   selecting the set of processed images from the processed images, wherein the set of processed images includes processed images obtained corresponding to at least some of the plurality of synthesis cycles;
   using the trained CNN, generating a feature map based on the set of the processed images, the feature map representing clusters of fluorescent signals represented in the set of processed images; and
   detecting the center positions of the clusters of the fluorescent signals by performing local maxima operations of the feature map.

5. The method of claim 4, wherein the trained CNN comprises one or more convolution and activation layers, one or more down sampling layers, one or more up sampling layers, and one or more skip connections.

6. The method of claim 1, wherein the trained CNN is a first trained CNN, and wherein extracting features from the set of the processed images based on the center positions of the clusters of fluorescent signals comprises:
   selecting a window size for extracting the features; and
   generating feature embedding vectors by applying the selected window size to the set of processed images using a second trained CNN, wherein the set of processed images includes images obtained in at least some of the plurality of synthesis cycles.

7. The method of claim 1, wherein determining, in parallel, the plurality of sequences of nucleic acid molecules using the extracted features based on the trained attention-based neural network comprises:
   providing the feature embedding vectors to the trained attention-based neural network;
   estimating, by the trained attention-based neural network using the feature embedding vectors, probabilities of bases corresponding to the clusters of fluorescent signals; and
   determining the plurality of sequences based on the probabilities of bases corresponding to the clusters of fluorescent signals.

8. The method of claim 1, wherein the trained attention-based neural network comprises one or more self-attention based encoders and one or more self-attention based decoders.

9. The method of claim 8, wherein a self-attention based decoder of the one or more self-attention based decoders comprises a masked multi-head attention layer, a multi-head attention layer, a multilayer perceptron layer, and one or more normalization layers.

10. The method of claim 8, wherein a self-attention based encoder of the one or more self-attention based encoders comprises a multi-head attention layer, a multilayer perceptron layer, and one or more normalization layers.

11. The method of claim 1, wherein the trained attention-based neural network comprises one or more self-attention based encoders without a decoder.

12. The method of claim 11, wherein determining, in parallel, the plurality of sequences of nucleic acid molecules using the extracted features based on the trained attention-based neural network comprises:
   providing the feature embedding vectors to the trained attention-based neural network, the feature embedding vectors representing signal intensities of a current synthesis cycle and a plurality of neighboring synthesis cycles;
   estimating, by the trained attention-based neural network using the feature embedding vectors, probabilities of bases corresponding to the clusters of fluorescent signals of the current synthesis cycle; and determining the plurality of sequences of nucleic acid molecules based on the probabilities of bases corresponding to the clusters of fluorescent signals.

13. A non-transitory computer readable medium comprising a memory storing one or more instructions which, when executed by one or more processors of at least one computing device, cause the at least one computing device to determine a plurality of sequences of nucleic acid molecules in a sequencing-by-synthesis process by:

obtaining images of fluorescent signals obtained in a plurality of synthesis cycles, the images of fluorescent signals being associated with a plurality of different fluorescence channels;

preprocessing the images of fluorescent signals to obtain processed images by performing one or more of:

light correction of one or more of the images based on one or both of a Gamma correction and a homomorphic filtering, image registration of images obtained for different synthesis cycles of the plurality of synthesis cycles, image registration of images obtained using different fluorescence channels, and image enhancement of the images;

based on a set of the processed images, detecting center positions of clusters of the fluorescent signals using a trained convolutional neural network (CNN);

extracting, based on the center positions of the clusters of fluorescent signals, features from the set of the processed images to generate feature embedding vectors; and determining, in parallel, the plurality of sequences of nucleic acid molecules using the extracted features based on a trained attention-based neural network.

14. The computer readable medium of claim 13, wherein based on the set of the processed images, detecting the center positions of the clusters of the fluorescent signals using the trained convolutional neural network (CNN) comprises:

selecting the set of processed images from the processed images, wherein the set of processed images includes processed images obtained corresponding to at least some of the plurality of synthesis cycles;

using the trained CNN, generating a feature map based on the set of the processed images, the feature map representing clusters of fluorescent signals represented in the set of processed images; and detecting the center positions of the clusters of the fluorescent signals by performing local maxima operations of the feature map.

15. The computer readable medium of claim 14, wherein the trained CNN comprises one or more convolution and activation layers, one or more down sampling layers, one or more up sampling layers, and one or more skip connections.

16. The computer readable medium of claim 13, wherein the trained CNN is a first trained CNN, and wherein extracting features from the set of the processed images based on the center positions of the clusters of fluorescent signals comprises:

selecting a window size for extracting the features; and
generating feature embedding vectors by applying the selected window size to the set of processed images using a second trained CNN, wherein the set of processed images includes images obtained in at least some of the plurality of synthesis cycles.

17. The computer readable medium of claim 13, wherein determining, in parallel, the plurality of sequences of nucleic acid molecules using the extracted features based on the trained attention-based neural network comprises:

providing the feature embedding vectors to the trained attention-based neural network;

estimating, by the trained attention-based neural network using the feature embedding vectors, probabilities of bases corresponding to the clusters of fluorescent signals; and determining the plurality of sequences based on the probabilities of bases corresponding to the clusters of fluorescent signals.

18. The computer readable medium of claim 13, wherein the trained attention-based neural network comprises one or more self-attention based encoders without a decoder.

19. The computer readable medium of claim 18, wherein determining, in parallel, the plurality of sequences of nucleic acid molecules using the extracted features based on the trained attention-based neural network comprises:

providing the feature embedding vectors to the trained attention-based neural network, the feature embedding vectors representing signal intensities of a current synthesis cycle and a plurality of neighboring synthesis cycles;

estimating, by the trained attention-based neural network using the feature embedding vectors, probabilities of bases corresponding to the clusters of fluorescent signals of the current synthesis cycle; and determining the plurality of sequences of nucleic acid molecules based on the probabilities of bases corresponding to the clusters of fluorescent signals.

20. A system for determining a plurality of sequences of nucleic acid molecules in a sequencing-by-synthesis process, the system comprises:

one or more processors of at least one computing device; and a memory storing one or more instructions, when executed by the one or more processors, cause the one or more processors to:

obtain images of fluorescent signals obtained in a plurality of synthesis cycles, the images of fluorescent signals being associated with a plurality of different fluorescence channels;

preprocess the images of fluorescent signals to obtain processed images by performing one or more of:

light correction of one or more of the images based on one or both of a Gamma correction and a homomorphic filtering, image registration of images obtained for different synthesis cycles of the plurality of synthesis cycles, image registration of images obtained using different fluorescence channels, and image enhancement of the images;

based on a set of the processed images, detect center positions of clusters of the fluorescent signals using a trained convolutional neural network (CNN);

extract, based on the center positions of the clusters of fluorescent signals, features from the set of the processed images to generate feature embedding vectors; and determine, in parallel, the plurality of sequences of nucleic acid molecules using the extracted features based on a trained attention-based neural network.

21. The system of claim 20, wherein based on the set of the processed images, detecting the center positions of the clusters of the fluorescent signals using the trained convolutional neural network (CNN) comprises:

selecting the set of processed images from the processed images, wherein the set of processed images includes processed images obtained corresponding to at least some of the plurality of synthesis cycles;

using the trained CNN, generating a feature map based on the set of the processed images, the feature map representing clusters of fluorescent signals represented in the set of processed images; and detecting the center positions of the clusters of the fluorescent signals by performing local maxima operations of the feature map.

22. The system of claim 21, wherein the trained CNN comprises one or more convolution and activation layers, one or more down sampling layers, one or more up sampling layers, and one or more skip connections.

23. The system of claim 20, wherein the trained CNN is a first trained CNN, and wherein extracting features from the set of the processed images based on the center positions of the clusters of fluorescent signals comprises:

selecting a window size for extracting the features; and generating feature embedding vectors by applying the selected window size to the set of processed images using a second trained CNN, wherein the set of processed images includes images obtained in at least some of the plurality of synthesis cycles.

24. The system of claim 20, wherein determining, in parallel, the plurality of sequences of nucleic acid molecules using the extracted features based on the trained attention-based neural network comprises:

providing the feature embedding vectors to the trained attention-based neural network;

estimating, by the trained attention-based neural network using the feature embedding vectors, probabilities of bases corresponding to the clusters of fluorescent signals; and determining the plurality of sequences based on the probabilities of bases corresponding to the clusters of fluorescent signals.

25. The system of claim 20, wherein the trained attention-based neural network comprises one or more self-attention based encoders without a decoder.

26. The system of claim 25, wherein determining, in parallel, the plurality of sequences of nucleic acid molecules using the extracted features based on the trained attention-based neural network comprises:

providing the feature embedding vectors to the trained attention-based neural network, the feature embedding vectors representing signal intensities of a current synthesis cycle and a plurality of neighboring synthesis cycles;

estimating, by the trained attention-based neural network using the feature embedding vectors, probabilities of bases corresponding to the clusters of fluorescent signals of the current synthesis cycle; and determining the plurality of sequences of nucleic acid molecules based on the probabilities of bases corresponding to the clusters of fluorescent signals.

\* \* \* \* \*